United States Patent
Chu

(10) Patent No.: US 9,078,728 B2
(45) Date of Patent: Jul. 14, 2015

(54) DEVICES AND METHODS FOR DELIVERING FEMALE PELVIC FLOOR IMPLANTS

(75) Inventor: Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1225 days.

(21) Appl. No.: 12/341,413

(22) Filed: Dec. 22, 2008

(65) Prior Publication Data
US 2009/0171140 A1    Jul. 2, 2009

Related U.S. Application Data

(60) Provisional application No. 61/017,210, filed on Dec. 28, 2007.

(51) Int. Cl.
*A61F 2/00* (2006.01)
*A61B 17/04* (2006.01)
*A61B 17/06* (2006.01)
*A61B 17/00* (2006.01)

(52) U.S. Cl.
CPC ........... *A61F 2/0045* (2013.01); *A61B 17/0482* (2013.01); *A61B 17/06109* (2013.01); *A61B 17/0485* (2013.01); *A61B 2017/00805* (2013.01); *A61B 2017/0472* (2013.01); *A61B 2017/06042* (2013.01); *A61B 2017/06071* (2013.01)

(58) Field of Classification Search
USPC ......... 600/37, 29, 30; 128/897–899; 606/151, 606/228, 232
See application file for complete search history.

(56) References Cited

U.S. PATENT DOCUMENTS

| 669,034 A | 2/1901 | Manly |
|---|---|---|
| 3,123,077 A | 3/1964 | Alcamo |
| 4,324,331 A | 4/1982 | Ignasiak |
| 4,429,695 A | 2/1984 | Green |
| 4,775,380 A | 10/1988 | Seedhom |

(Continued)

FOREIGN PATENT DOCUMENTS

| EP | 0412664 A1 | 2/1991 |
|---|---|---|
| EP | 1 201 189 A2 | 5/2002 |

(Continued)

OTHER PUBLICATIONS

International Search Report and Written Opinion for PCT/US08/88129, mailed on Jul. 6, 2009; 15 pages.

(Continued)

*Primary Examiner* — Catherine B Kuhlman
*Assistant Examiner* — Shannon McBride

(57) ABSTRACT

In one embodiment, an apparatus includes an elongate body that defines a lumen and a suture coupled to the elongate body and at least partially disposed within the lumen. The suture extends at least partially from a proximal end of the elongate body and forms a loop configured to couple a portion of a pelvic implant to the elongate body. In another embodiment, an apparatus includes an elongate body having a distal end configured to releasably couple the elongate body to a delivery device. A tubular member is movably disposed over at least a portion of the elongate body. A coupler is disposed at a proximal end of the elongate body and is configured to releasably couple an implant to the elongate body. The tubular member can be slidably disposed over at least a portion of the implant when the pelvic implant is coupled to the elongate body.

18 Claims, 29 Drawing Sheets

(56) References Cited

U.S. PATENT DOCUMENTS

| | | |
|---|---|---|
| 4,792,336 A | 12/1988 | Hlavacek et al. |
| 4,919,667 A | 4/1990 | Richmond |
| 4,935,027 A | 6/1990 | Yoon |
| 4,998,912 A | 3/1991 | Scarbrough et al. |
| 5,013,292 A | 5/1991 | Lemay |
| 5,082,112 A | 1/1992 | Dunklee |
| 5,108,406 A | 4/1992 | Lee |
| 5,149,329 A | 9/1992 | Richardson |
| 5,217,466 A | 6/1993 | Hasson |
| 5,217,486 A | 6/1993 | Rice et al. |
| 5,217,494 A | 6/1993 | Coggins et al. |
| 5,263,969 A | 11/1993 | Phillips |
| 5,356,432 A | 10/1994 | Rutkow et al. |
| 5,362,294 A | 11/1994 | Seitzinger |
| 5,383,905 A | 1/1995 | Golds et al. |
| 5,405,359 A | 4/1995 | Pierce |
| 5,413,268 A | 5/1995 | Green et al. |
| 5,425,747 A | 6/1995 | Brotz |
| 5,458,636 A | 10/1995 | Brancato |
| 5,485,917 A | 1/1996 | Early |
| 5,505,363 A | 4/1996 | Green et al. |
| 5,534,008 A | 7/1996 | Acksel |
| 5,562,678 A | 10/1996 | Booker |
| 5,562,689 A | 10/1996 | Green et al. |
| 5,584,859 A | 12/1996 | Brotz |
| 5,643,311 A | 7/1997 | Smith et al. |
| 5,683,402 A | 11/1997 | Cosgrove et al. |
| 5,702,397 A | 12/1997 | Goble et al. |
| 5,741,277 A | 4/1998 | Gordon et al. |
| 5,752,644 A | 5/1998 | Bolanos et al. |
| 5,840,011 A | 11/1998 | Landgrebe et al. |
| 5,865,361 A | 2/1999 | Milliman et al. |
| 5,899,909 A | 5/1999 | Claren et al. |
| 5,931,855 A | 8/1999 | Buncke |
| 5,948,001 A | 9/1999 | Larsen |
| 5,976,127 A | 11/1999 | Lax |
| 6,010,447 A | 1/2000 | Kardjian |
| 6,012,580 A | 1/2000 | Peters et al. |
| 6,039,686 A | 3/2000 | Kovac |
| 6,042,534 A | 3/2000 | Gellman et al. |
| 6,042,536 A | 3/2000 | Tihon et al. |
| 6,042,592 A | 3/2000 | Schmitt |
| 6,044,847 A | 4/2000 | Carter et al. |
| 6,197,036 B1 | 3/2001 | Tripp et al. |
| 6,200,330 B1 | 3/2001 | Benderev et al. |
| 6,221,005 B1 | 4/2001 | Bruckner et al. |
| 6,267,772 B1 | 7/2001 | Mulhauser et al. |
| 6,273,852 B1 | 8/2001 | Lehe et al. |
| 6,306,079 B1 | 10/2001 | Trabucco |
| 6,322,492 B1 | 11/2001 | Kovac |
| 6,328,686 B1 | 12/2001 | Kovac |
| 6,375,662 B1 | 4/2002 | Schmitt |
| 6,382,214 B1 | 5/2002 | Raz |
| 6,406,423 B1 | 6/2002 | Scetbon |
| 6,478,727 B2 | 11/2002 | Scetbon |
| 6,491,703 B1 | 12/2002 | Ulmsten |
| 6,502,578 B2 | 1/2003 | Raz et al. |
| 6,506,190 B1 | 1/2003 | Walshe |
| 6,544,273 B1 | 4/2003 | Harari et al. |
| 6,547,800 B2 | 4/2003 | Foerster et al. |
| 6,565,580 B1 | 5/2003 | Beretta |
| 6,575,998 B2 | 6/2003 | Beyar |
| 6,582,443 B2 | 6/2003 | Cabak et al. |
| 6,592,515 B2 | 7/2003 | Thierfelder et al. |
| 6,592,610 B2 | 7/2003 | Beyar |
| 6,595,911 B2 | 7/2003 | LoVuolo |
| 6,596,001 B2 | 7/2003 | Stormby et al. |
| 6,599,235 B2 | 7/2003 | Kovac |
| 6,599,310 B2 | 7/2003 | Leung et al. |
| 6,612,977 B2 | 9/2003 | Staskin et al. |
| 6,638,209 B2 | 10/2003 | Landgrebe |
| 6,638,210 B2 | 10/2003 | Berger |
| 6,638,211 B2 | 10/2003 | Suslian et al. |
| 6,641,524 B2 | 11/2003 | Kovac |
| 6,641,525 B2 | 11/2003 | Rocheleau et al. |
| 6,648,899 B2 | 11/2003 | Kalinski et al. |
| 6,648,921 B2 | 11/2003 | Anderson et al. |
| 6,652,450 B2 | 11/2003 | Neisz et al. |
| 6,666,817 B2 | 12/2003 | Li |
| 6,669,706 B2 | 12/2003 | Schmitt et al. |
| 6,669,735 B1 | 12/2003 | Pelissier |
| 6,673,010 B2 | 1/2004 | Skiba et al. |
| 6,691,711 B2 | 2/2004 | Raz et al. |
| 6,695,855 B1 | 2/2004 | Gaston |
| 6,702,827 B1 | 3/2004 | Lund et al. |
| 6,730,110 B1 | 5/2004 | Harari et al. |
| 6,746,455 B2 | 6/2004 | Beyar et al. |
| 6,752,814 B2 | 6/2004 | Gellman et al. |
| 6,755,781 B2 | 6/2004 | Gellman |
| 6,808,487 B2 | 10/2004 | Migliari |
| 6,830,052 B2 | 12/2004 | Carter et al. |
| 6,848,152 B2 | 2/2005 | Genova et al. |
| 6,881,184 B2 | 4/2005 | Zappala |
| 6,890,338 B1 | 5/2005 | Davis et al. |
| 6,908,425 B2 | 6/2005 | Luscombe |
| 6,911,003 B2 | 6/2005 | Anderson et al. |
| 6,911,034 B2 | 6/2005 | Nobles et al. |
| 6,932,759 B2 | 8/2005 | Kammerer et al. |
| 6,936,052 B2 | 8/2005 | Gellman et al. |
| 6,946,003 B1 | 9/2005 | Wolowacz et al. |
| 6,953,428 B2 | 10/2005 | Gellman et al. |
| 6,960,160 B2 | 11/2005 | Browning |
| 6,971,986 B2 | 12/2005 | Staskin et al. |
| 6,991,597 B2 | 1/2006 | Gellman et al. |
| 7,011,688 B2 | 3/2006 | Gryska et al. |
| 7,025,772 B2 | 4/2006 | Gellman et al. |
| 7,048,682 B2 | 5/2006 | Neisz et al. |
| 7,056,333 B2 | 6/2006 | Walshe |
| 7,070,556 B2 | 7/2006 | Anderson et al. |
| 7,070,558 B2 | 7/2006 | Gellman et al. |
| 7,083,568 B2 | 8/2006 | Neisz et al. |
| 7,083,637 B1 | 8/2006 | Tannhauser |
| 7,090,686 B2 | 8/2006 | Nobles et al. |
| 7,094,199 B2 | 8/2006 | Petros et al. |
| 7,112,171 B2 | 9/2006 | Rocheleau et al. |
| 7,112,210 B2 | 9/2006 | Ulmsten et al. |
| 7,122,039 B2 | 10/2006 | Chu |
| 7,131,943 B2 | 11/2006 | Kammerer |
| 7,131,944 B2 | 11/2006 | Jacquetin |
| 7,198,597 B2 | 4/2007 | Siegel et al. |
| 7,204,801 B2 | 4/2007 | Grocela |
| 7,204,802 B2 | 4/2007 | De Leval |
| 7,223,229 B2 | 5/2007 | Inman et al. |
| 7,226,407 B2 | 6/2007 | Kammerer et al. |
| 7,226,408 B2 | 6/2007 | Harai et al. |
| 7,229,453 B2 | 6/2007 | Anderson et al. |
| 7,235,043 B2 | 6/2007 | Gellman et al. |
| 7,244,260 B2 | 7/2007 | Koseki |
| 7,244,759 B2 | 7/2007 | Muller et al. |
| 7,267,645 B2 | 9/2007 | Anderson et al. |
| 7,291,104 B2 | 11/2007 | Neisz et al. |
| 7,351,197 B2 | 4/2008 | Montpetit et al. |
| 7,361,138 B2 | 4/2008 | Wagner et al. |
| 7,364,541 B2 | 4/2008 | Chu et al. |
| 7,402,133 B2 | 7/2008 | Chu et al. |
| 7,413,540 B2 | 8/2008 | Gellman et al. |
| 7,722,527 B2 * | 5/2010 | Bouchier et al. ............ 600/30 |
| 2002/0010457 A1 | 1/2002 | Duchon |
| 2002/0091373 A1 | 7/2002 | Berger |
| 2002/0128670 A1 | 9/2002 | Ulmsten et al. |
| 2002/0147382 A1 * | 10/2002 | Neisz et al. ............ 600/29 |
| 2002/0151909 A1 | 10/2002 | Gellman et al. |
| 2002/0156489 A1 | 10/2002 | Gellman et al. |
| 2003/0125715 A1 | 7/2003 | Kuehn et al. |
| 2003/0149334 A1 | 8/2003 | Ulmsten et al. |
| 2003/0220538 A1 | 11/2003 | Jacquetin |
| 2003/0225424 A1 | 12/2003 | Benderev |
| 2004/0006353 A1 | 1/2004 | Bosley et al. |
| 2004/0039453 A1 | 2/2004 | Anderson et al. |
| 2004/0073234 A1 | 4/2004 | Chu et al. |
| 2004/0106847 A1 | 6/2004 | Benderev et al. |
| 2004/0181243 A1 | 9/2004 | Chu et al. |
| 2004/0225181 A1 | 11/2004 | Chu et al. |
| 2004/0230206 A1 | 11/2004 | Gellman et al. |

(56) References Cited

U.S. PATENT DOCUMENTS

| | | |
|---|---|---|
| 2005/0004427 A1 | 1/2005 | Cervigni |
| 2005/0004576 A1 | 1/2005 | Benderev |
| 2005/0038451 A1 | 2/2005 | Rao et al. |
| 2005/0038452 A1 | 2/2005 | Chu |
| 2005/0075660 A1 | 4/2005 | Chu et al. |
| 2005/0080317 A1 | 4/2005 | Merade |
| 2005/0090706 A1 | 4/2005 | Gellman et al. |
| 2005/0096499 A1 | 5/2005 | Li et al. |
| 2005/0101834 A1 | 5/2005 | Merade |
| 2005/0107660 A1 | 5/2005 | Valtchev |
| 2005/0107805 A1 | 5/2005 | Bouffier et al. |
| 2005/0131391 A1 | 6/2005 | Chu et al. |
| 2005/0131392 A1 | 6/2005 | Chu et al. |
| 2005/0131393 A1 | 6/2005 | Chu et al. |
| 2005/0177022 A1 | 8/2005 | Chu et al. |
| 2005/0192600 A1 | 9/2005 | Nicolo et al. |
| 2005/0245787 A1 | 11/2005 | Cox et al. |
| 2005/0250978 A1 | 11/2005 | Kammerer |
| 2005/0256366 A1 * | 11/2005 | Chu ................ 600/30 |
| 2005/0256530 A1 | 11/2005 | Petros |
| 2005/0261547 A1 | 11/2005 | Bouffier |
| 2005/0277807 A1 | 12/2005 | MacLean et al. |
| 2006/0015001 A1 | 1/2006 | Staskin et al. |
| 2006/0025649 A1 | 2/2006 | Smith et al. |
| 2006/0025783 A1 | 2/2006 | Smith et al. |
| 2006/0041185 A1 | 2/2006 | Browning |
| 2006/0058574 A1 | 3/2006 | Priewe et al. |
| 2006/0058575 A1 | 3/2006 | Zaddem et al. |
| 2006/0069301 A1 | 3/2006 | Neisz et al. |
| 2006/0089524 A1 | 4/2006 | Chu |
| 2006/0089525 A1 | 4/2006 | Mamo et al. |
| 2006/0122457 A1 | 6/2006 | Kovac et al. |
| 2006/0173237 A1 | 8/2006 | Jacquetin |
| 2006/0195010 A1 | 8/2006 | Arnal |
| 2006/0205995 A1 | 9/2006 | Browning |
| 2006/0211911 A1 | 9/2006 | Jao et al. |
| 2006/0229596 A1 | 10/2006 | Weiser et al. |
| 2006/0260618 A1 | 11/2006 | Hodroff |
| 2006/0264698 A1 | 11/2006 | Kondonis et al. |
| 2006/0287571 A1 | 12/2006 | Gozzi et al. |
| 2007/0015953 A1 | 1/2007 | Maclean |
| 2007/0123915 A1 | 5/2007 | Kammerer et al. |
| 2007/0203508 A1 | 8/2007 | White et al. |
| 2007/0276358 A1 | 11/2007 | Barzell et al. |
| 2008/0091221 A1 | 4/2008 | Brubaker et al. |
| 2009/0171142 A1 | 7/2009 | Chu |
| 2009/0221867 A1 * | 9/2009 | Ogdahl et al. ................ 600/37 |
| 2010/0268018 A1 | 10/2010 | Chu |

FOREIGN PATENT DOCUMENTS

| | | |
|---|---|---|
| EP | 1 508 305 A2 | 2/2005 |
| EP | 1520554 A2 | 6/2005 |
| EP | 1563794 A1 | 8/2005 |
| GB | 670349 A | 4/1952 |
| WO | 98/35632 A1 | 8/1998 |
| WO | 02/078571 A2 | 10/2002 |
| WO | 03059174 A2 | 7/2003 |
| WO | 03/092546 A2 | 11/2003 |
| WO | 03/096929 A1 | 11/2003 |
| WO | 2004/091442 A2 | 10/2004 |
| WO | 2005/110274 A2 | 11/2005 |
| WO | WO 2005/122721 A2 | 12/2005 |
| WO | WO 2006/046950 A1 | 5/2006 |
| WO | 2006/069078 A2 | 6/2006 |
| WO | 2006/108045 A2 | 10/2006 |
| WO | 2007019374 A2 | 2/2007 |
| WO | 20070019274 A | 2/2007 |
| WO | WO 2007/016698 A2 | 2/2007 |
| WO | WO 2007/019274 A2 | 2/2007 |
| WO | WO 2007/019374 A2 | 2/2007 |
| WO | WO 2007/059199 A2 | 5/2007 |
| WO | WO 2007059368 A1 * | 5/2007 |
| WO | 2007/097994 A2 | 8/2007 |
| WO | 2007/149348 A2 | 12/2007 |
| WO | 2009/086369 A2 | 7/2009 |

OTHER PUBLICATIONS

International Preliminary Report on Patentability for PCT Patent Application No. PCT/US2008/088129, mailed on Jul. 8, 2010, 11 pages.

Communication Relating to the Results of the Partial International Search for PCT/US08/88129, mailed on Mar. 26, 2009; 2 pages.

Non Final Office Action for U.S. Appl. No. 12/341,695, mailed Dec. 9, 2011, 19 pages.

Office Action Response for U.S. Appl. No. 12/341,695, filed Oct. 11, 2011, 4 pages.

Office Action for U.S. Appl. No. 12/341,695, mailed Sep. 9, 2011, 7 pages.

Non Final Office Action for U.S. Appl. No. 12/341,695, mailed May 10, 2012, 11 pages.

International Preliminary Report on Patentability for PCT Application No. PCT/US2008/088152, mailed on Jul. 8, 2010, 11 pages.

International Search Report and Written Opinion for PCT Application No. PCT/US2008/088152, mailed on Dec. 11, 2009, 5 pages.

Notice of Allowance for U.S. Appl. No. 12/341,695, mailed Jan. 4, 2013, 10 pages.

Non-Final Office Action for U.S. Appl. No. 12/341,695, mailed Aug. 30, 2012, 12 pages.

Final Office Action Response for U.S. Appl. No. 12/341,695, filed Aug. 8, 2012, 7 pages.

Non-Final Office Action Response for U.S. Appl. No. 12/341,695, filed Nov. 30, 2012, 7 pages.

Restriction Requirement for U.S. Appl. No. 13/867,460, mailed Jul. 15, 2014, 7 pages.

Communication Pursuant to Article 94(3) for EP Application No. 08867530.1, mailed Jul. 15, 2014, 5 pages.

Office Action for EP Application No. 08867530.1, mailed Feb. 25, 2015, 5 pages.

* cited by examiner

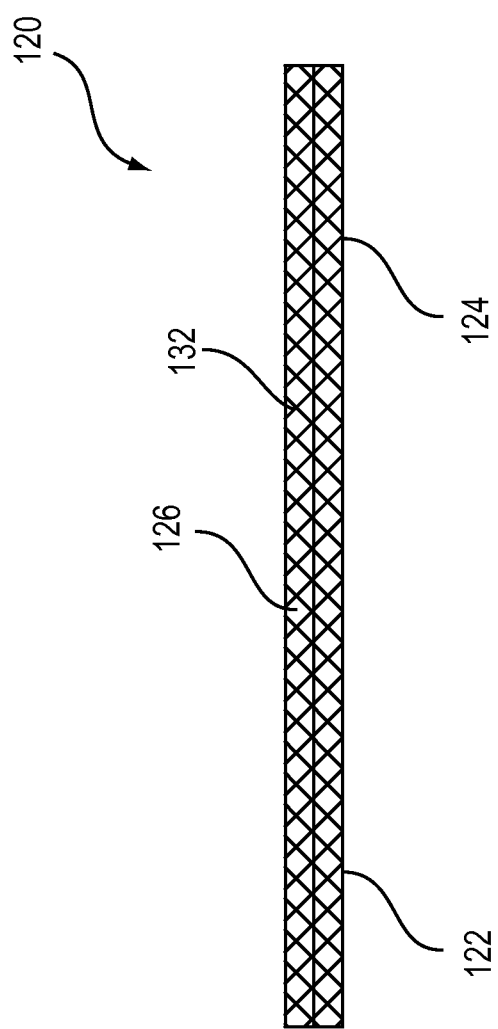

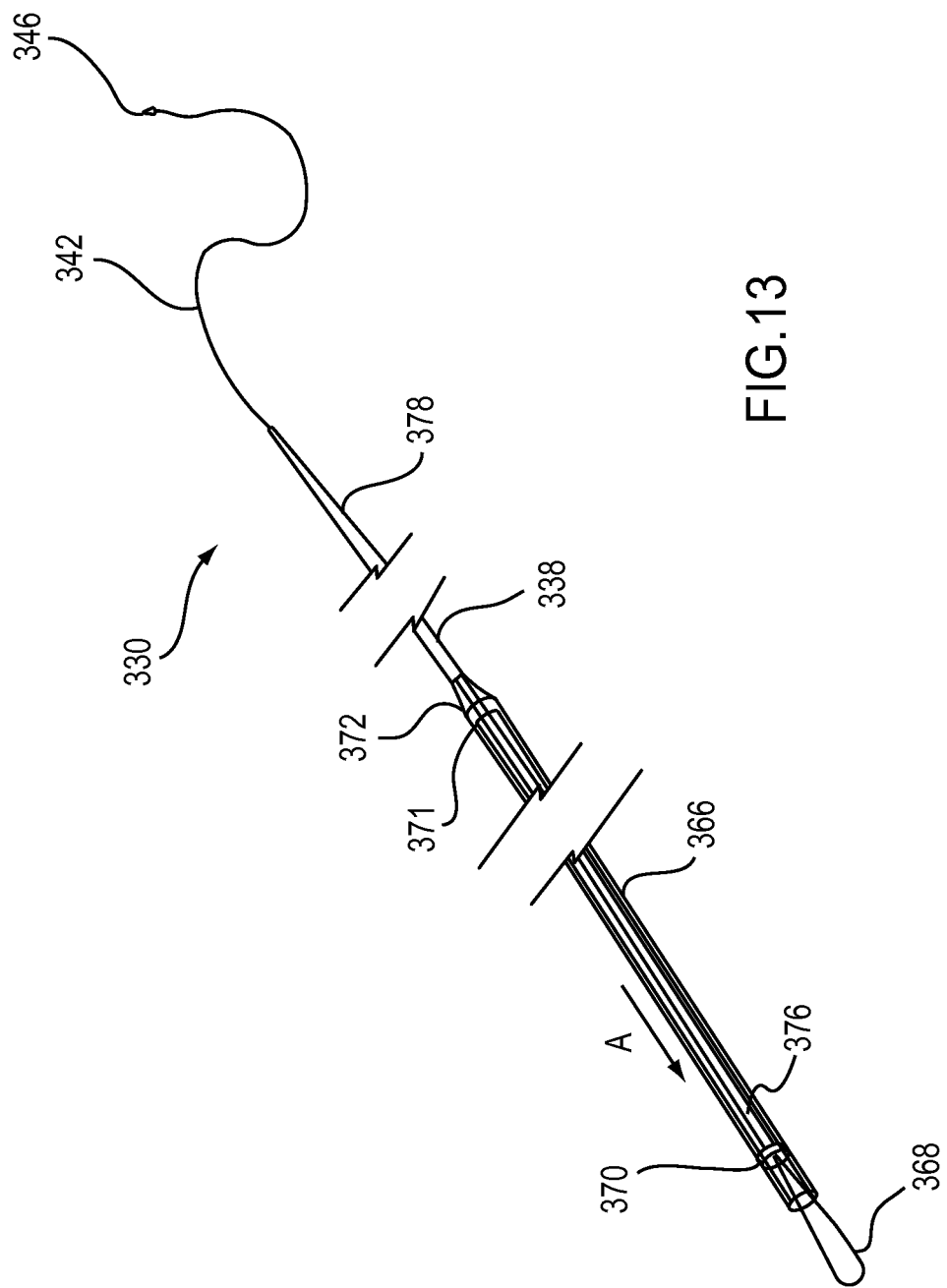

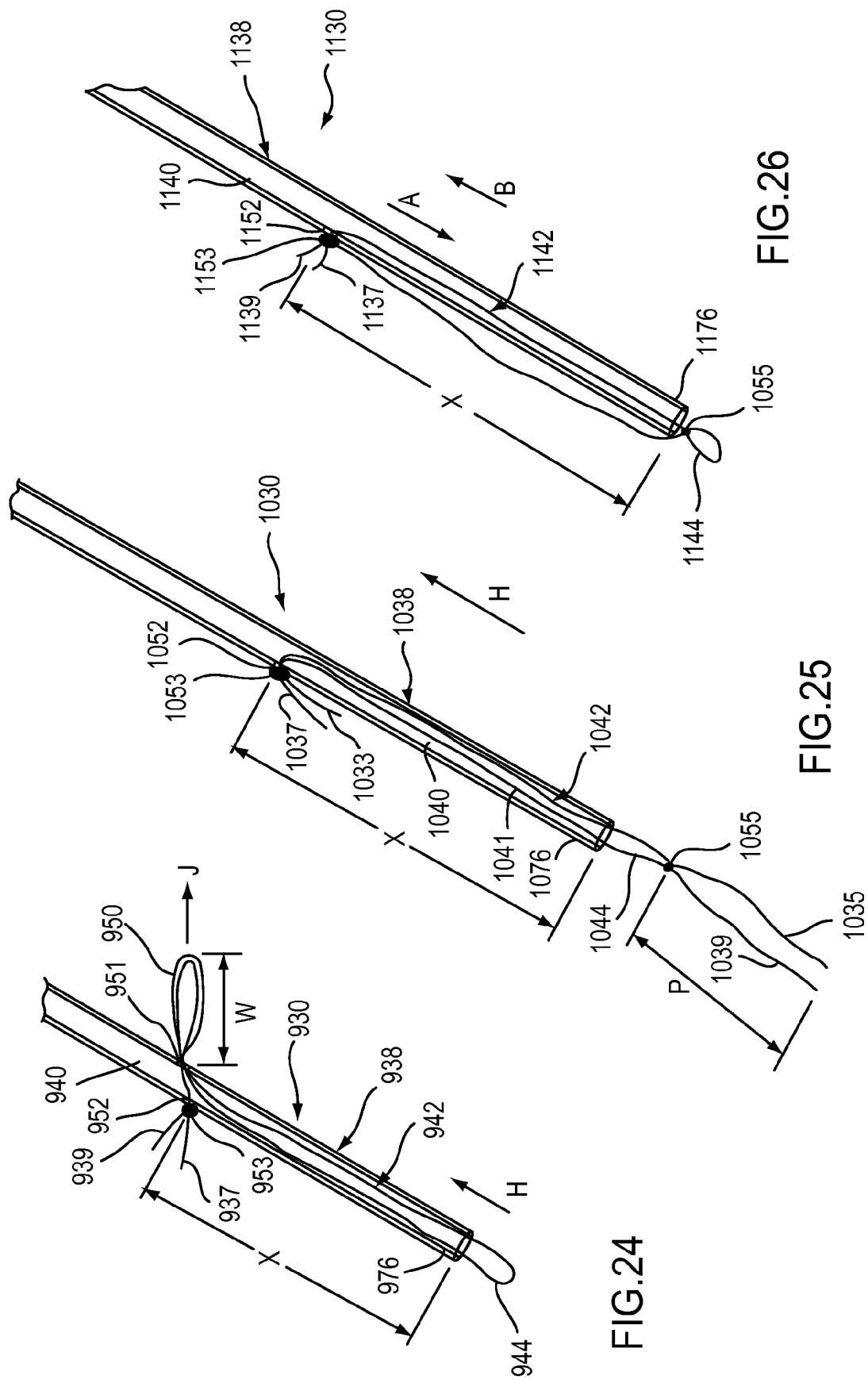

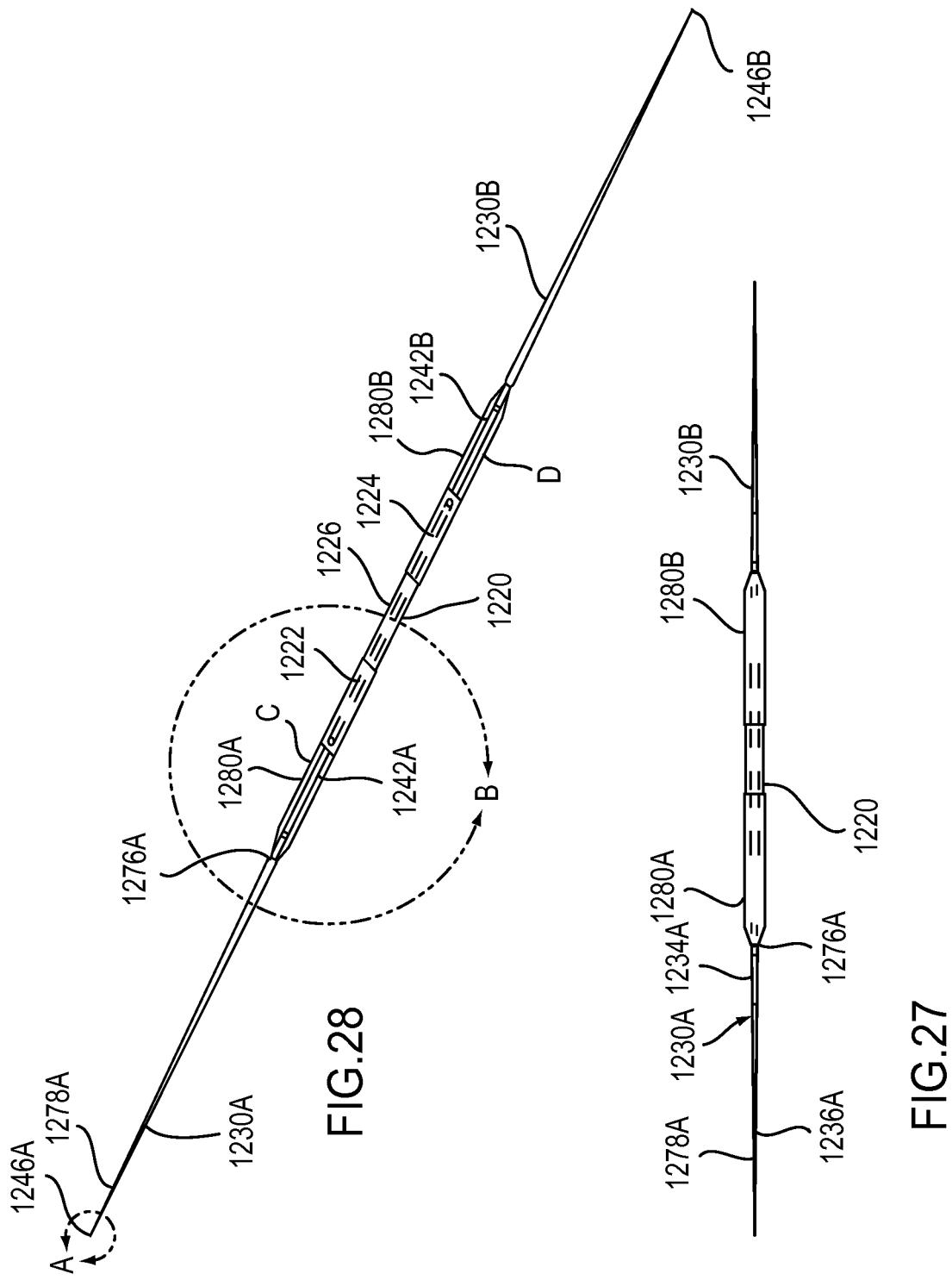

DEVICES AND METHODS FOR DELIVERING FEMALE PELVIC FLOOR IMPLANTS

CROSS-REFERENCE TO RELATED APPLICATIONS

This application claims priority to U.S. Provisional Patent Application Ser. No. 61/017,210, entitled "Devices and Methods for Delivering Female Pelvic Floor Implants," filed Dec. 28, 2007, the disclosure of which is hereby incorporated by reference in its entirety.

BACKGROUND

The disclosed invention relates generally to medical devices and more particularly to devices and methods for delivering an implant within a pelvic region to treat various female pelvic dysfunctions.

A variety of medical procedures are performed to treat various female pelvic dysfunctions, including procedures to treat urinary incontinence, and correcting various conditions, such as, uterine prolapse, cystoceles, rectoceles, and vaginal vault prolapse.

A vaginal prolapse can be caused due to age or other factors and typically results in one of three types of prolapse: hysterocele, cystocele, and rectocele. A hysterocele occurs when the uterus descends into the vagina and is often treated with a hysterectomy followed by a vaginal vault suspension. A cystocele occurs when the bladder bulges or descends into the vagina and a rectocele occurs when the rectum bulges or descends into the vagina. It is often common for multiple prolapses to occur at the same time. Treatment of vaginal prolapse can include a suturing procedure or the use of an implant for support or suspension.

Various devices and procedures are used to deliver and secure pelvic implants within a variety of different anatomical structures within a pelvic region. Implants can be delivered to a pelvic region through a single vaginal incision, and/or through exterior incisions in the patient. Various complications can occur due to, for example, space constraints for performing an implantation procedure. Often, implants can become damaged during delivery due to the type of delivery device and/or the type of implant, or due to excessive handling of the implant during the implant procedure. Thus, it would be desirable to improve the delivery process associated with a pelvic implant to help prevent damage to the implant during implantation.

Thus, a need exists for devices and methods for delivering pelvic implants to treat various pelvic dysfunctions that provide improved coordination and organization of the placement of an implant and/or reduce damage to the implant during delivery.

SUMMARY OF THE INVENTION

An apparatus according to an embodiment of the invention includes an elongate body that defines a lumen. A suture is coupled to the elongate body and at least partially disposed within the lumen of the elongate body. The suture extends at least partially from a proximal end of the elongate body and forms a loop configured to couple a portion of a pelvic implant to the elongate body. An apparatus according to another embodiment includes an elongate body having a distal end configured to releasably couple the elongate body to a delivery device. A tubular member is movably disposed over at least a portion of the elongate body. A coupler is disposed at a proximal end of the elongate body and is configured to releasably couple a pelvic implant to the elongate body. The tubular member is configured to be slidably disposed over at least a portion of the pelvic implant when the pelvic implant is coupled to the elongate body.

BRIEF DESCRIPTION OF THE DRAWINGS

FIGS. 2 and 2A are each a top view of a different embodiment of an implant.

FIG. 13 is a side perspective view of another embodiment of a dilator device.

FIGS. 21-26 are each a side perspective view of a portion of a dilator device according to different embodiments.

FIG. 27 is a top view of an embodiment of an implant and dilator assembly.

FIG. 28 is a side perspective view of the implant and dilator assembly of FIG. 27.

DETAILED DESCRIPTION

Figure 1:
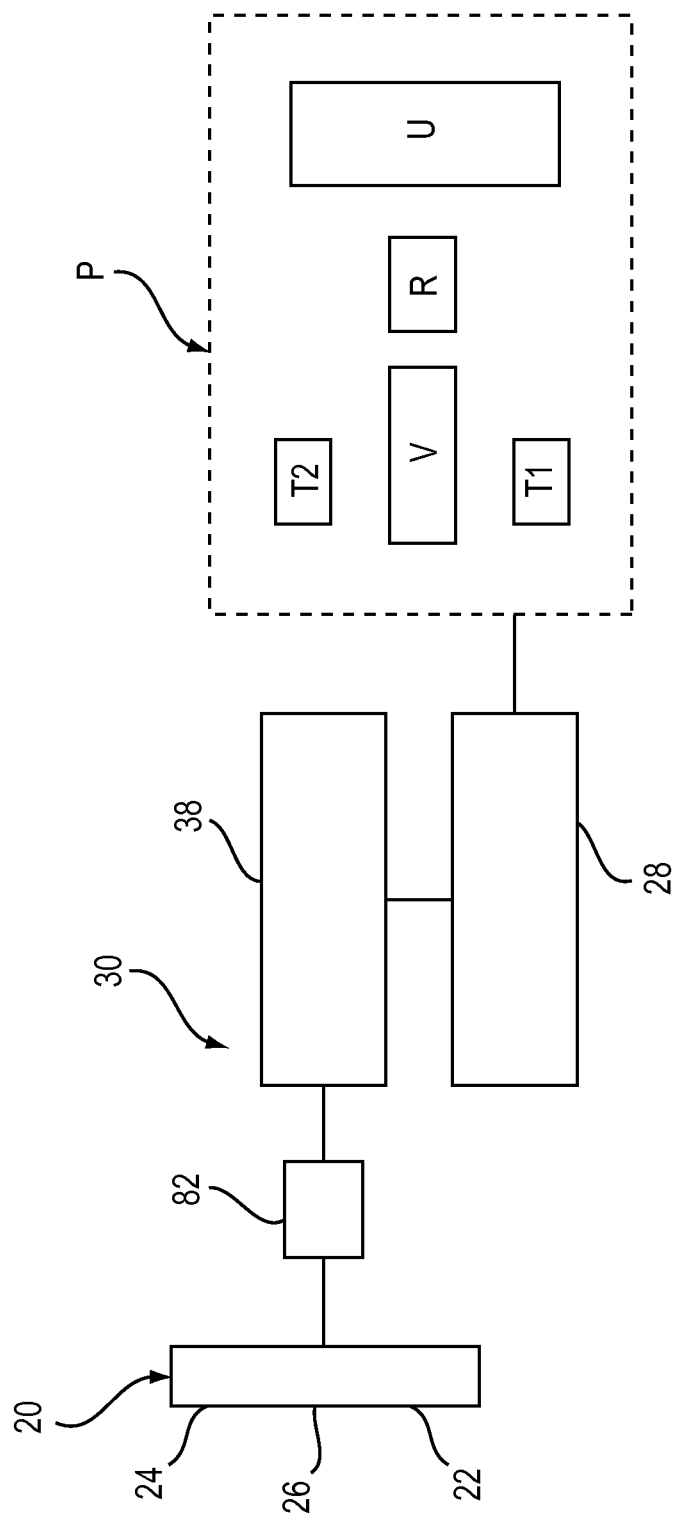
FIG. 1 is a schematic illustration of an embodiment of a delivery devices and an embodiment of an implant, and a schematic illustration of a pelvic region.

The devices and methods described herein are generally directed to the delivery and placement of an implant (e.g., a urethral sling, a uterine support device) to an anatomical site within a patient. For example, the devices and methods are suitable for delivering an implant to a pelvic region of a patient. An implant can be placed into the pelvic space of a patient and secured at several different locations within the pelvic space, to treat many different female pelvic floor dysfunctions. For example, an implant can be secured to a sacrospinous ligament or a ureterosacral ligament for uterine preservation. In another embodiment, an implant can be secured to pubo-urethral tissue or obturator fossa to treat, for example, incontinence. In yet another embodiment, an implant can be secured to an arcus tendineus fascia pelvic for paravaginal repairs including, for example, cystoceles, rectoceles and enteroceles. A single implant or multiple implants can be used in a single procedure. In some applications, when multiple implants are used, support can be provided in desired areas and improved control of the direction of stretch or support of the implant can be achieved. Various delivery devices are also described for delivering and securing an implant assembly within the patient.

An implant according to an embodiment of the invention can include a tanged portion and a detanged portion. The terms "tanged" or "tangs" as used herein mean roughened or jagged edges or areas, such as can result from cutting a woven or knit mesh material. The tanged portion can be used, for example, to anchor or secure the implant to tissue. An implant according to an embodiment of the invention can be implanted, for example, through a vaginal incision, and placed bilaterally in a direction toward an obturator muscle, or in a retro-pubic direction (behind the pubic bone), or in a pre-pubic direction (in front of the pubic bone). In other embodiments, an implant can be placed in the direction of other anatomical structures as desired. Although a single vaginal incision procedure for treating female pelvic floor dysfunctions is described herein, other procedures can be performed using the devices and methods described herein.

Various embodiments of a dilator device are also described herein. An implant can be releasably coupled to a dilator device and the dilator device can be releasably coupled to a delivery device and used to assist in the delivery of an implant to a pelvic region. For example, with an implant coupled to a dilator device, the dilator device can be passed through a tissue site using a delivery device. Because the implant is coupled to the dilator device, the implant will follow the path of the dilator. A portion of the implant can then remain within the tissue for anchoring. In some embodiments, a dilator can be used to lead an implant or a strap of an implant through a tissue in an intracorporeal location (i.e., within the patient's body), such as the sacrospinous ligament or arcus tendineus. In other embodiments, a dilator can be used to lead an implant or a strap of an implant through a tissue and to an extracorporeal location (outside the patient's body), such as through an obturator membrane or a retro-pubic approach and out through an exterior incision in the patient.

In some embodiments, an implant can be associated to a dilator device after the dilator has been placed within a pelvic region. For example, in an embodiment of an implant having multiple straps, such as with a pelvic floor repair implant, prior placement of the dilator can help with coordinating and organizing the placement of the various straps. Placing the dilator(s) within a pelvic region first also helps reduce handing of the implant which can reduce damage to the implant during an implantation procedure.

As used herein, the terms proximal portion or proximal end refer to the portion or end, respectively, of a device that is closest to a physician when performing a medical procedure, and the terms distal portion or distal end refer to the portion or end, respectively, of the device that is furthest from the physician during a medical procedure. For example, a distal end or portion of a dilator device as described herein refers to the end or portion of the dilator device that is first inserted into a body of a patient during a medical procedure. The proximal end or portion is the end or portion of the dilator that is inserted into a body of the patient after the distal end or portion.

FIG. 1 is a schematic illustration of various devices according to an embodiment of the invention and a schematic representation of a pelvic region of a patient. Specifically, FIG. 1 schematically illustrates an implant, a dilator device and a delivery device according to embodiments of the invention. An implant 20 (also referred to herein as implant member or sling) can be any of a variety of different types of pelvic implants used to treat various female pelvic dysfunctions. For example, the implant 20 can be a urethral sling, or an implant configured to support a uterus. One or more implants 20 can be implanted within a variety of different locations within a pelvic region of a patient. The implant 20 can be delivered through a single incision within a vagina of a patient and thereafter secured and/or deposited within pelvic tissue. Pelvic tissue can include, for example, ligaments, muscle, fascia, or any other structure or soft tissue within a pelvic region of a patient.

The implant 20 can be formed with a mesh material to allow tissue in-growth to the implant 20 after implantation. For example, the implant 20 can be formed with a mesh material as described in U.S. Patent Pub. 2005/0038452 A1 to Chu, the disclosure of which is hereby incorporated by reference in its entirety. In some embodiments, the entire implant 20 can be formed with a mesh material, whereas in other embodiments, only a portion of the implant 20 is formed with a mesh material. The implant 20 can be monolithically formed. Alternatively, the implant 20 can be formed with multiple different materials and/or can include multiple different components coupled together.

The implant 20 includes an elongate body having a first end portion 22, a second end portion 24, and a middle portion 26. The first and second end portions 22 and 24 can include tangs or a tanged portion to grip or attach to a tissue portion T1, T2 within a pelvic region P. The middle portion 26 can also include tangs or can be untanged. The middle portion 26 is also referred to as the support portion. The tangs allow the implant 20 to be anchored within pelvic tissue without the use of additional anchoring mechanisms or sutures. In some embodiments, an implant includes tangs on an edge along an entire length of the implant 20. In other embodiments, the implant 20 includes tangs covering substantially all of an exterior surface of the implant. In some embodiments, tangs are only on the end portions 22, 24 of the implant 20.

An implant 20 can be a variety of different shapes, sizes and configurations depending on the particular need and/or medical treatment. For example, the implant 20 can be substantially rectangular, square, oval, elliptical, etc. The implant 20 can be formed with various widths, lengths and thicknesses and the implant 20 can be uniformly formed (e.g., the same thickness and/or width) along the length of the implant 20. Alternatively, the dimensions of the implant 20, can vary along its length. For example, the ends of the implant 20 can be tapered. A length of the middle or support portion 26 of the implant 20 can be, for example, between 2 cm (0.8 inches) and 12 cm (4.7 inches). The end portions 22, 24 can each have a length, for example, between 2 cm (0.8 inches) and 4 cm (1.5 inches). In some embodiments, a width of the middle portion 26 is wider than the end portions 22, 24. The implant 20 can also be formed with one or more straps or arms as used in various pelvic floor repair procedures.

In some embodiments, the implant 20 can also include one or more strengthening members (not shown in FIG. 1). In some embodiments, the strengthening member is in the form of a heat seal on the implant 20. For example, strands of the implant can be selectively melted and bonded along a longitudinal axis of the implant to prevent stretching and/or unraveling of the implant 20 during implantation. The strengthening member can extend along an entire length of the implant, or only along a portion of the implant 20. Multiple strengthening members (e.g., heat seals) can be arranged in various patterns on the implant 20. The implant 20 can also include strengthening members that extend transverse to a longitudinal length of the implant 20.

An implant 20 can be coupled to various different tissues within the pelvic region P, such as, for example, a sacrospinous ligament, a tendineus arch of levator muscle (also referred to herein as "arcus tendineus" or "white line"), or to an iliococcygeus muscle, or to other anatomical securement sites within the pelvic region of a patient. For example, each of the ends 22, 24 of the implant 20 can be deposited at selected tissue sites T1 and T2 within the pelvic region P, such that the middle portion 26 of the implant 20 is positioned beneath a urethra R or a uterus U of the patient. The implant 20 can also be coupled to a vagina V of the patient, such as to the vaginal apex, to a wall of the vagina V, secured inside the vagina (e.g., within a vaginal lumen) or within the pelvic region. In some embodiments, the implant 20 can be used to support a uterus U of the patient. In some embodiments only one implant is implanted on one side of the pelvic region P. In other embodiments, more than one implant 20 is implanted, such as one implant assembly on contra lateral sides of the pelvic region of the patient. In yet other embodiments, the implant is sized to extend from one side of the pelvic region to the other side of the pelvic region.

The implant 20 can be delivered into the pelvic region P using a delivery device 28 together with one or more dilator devices 30. The delivery device 28 can be, for example, a Capio® Suture Capture Device or a Obtryx® Halo device, each of which are manufactured by Boston Scientific Corporation. Other types of devices can alternatively be used, such as, for example, the suturing device described in U.S. Patent Pub. 2004/0181243 A1 to Chu et al., entitled Re-shapeable Medical Device, the disclosure of which is hereby incorporated by reference in its entirety. The pelvic tissues T1 and T2 can be, for example, a sacrospinous ligament, a tendineus arch of levator muscle, an iliococcygeus muscle or other anatomical structure or tissue within a pelvis. The delivery device 28 can also be used to pass a suture end through a wall of a vagina or to pass a suture through the epithelium of a vaginal wall without passing the suture through the vaginal wall.

The dilator device 30 (also referred to herein as dilator) includes an elongate body 38 that has a distal end configured to be associated to a delivery device 28 and a proximal end configured to releasably couple an implant 20 thereto. For example, the dilator 30 can include a first coupling portion 82 on a proximal end configured to releasably couple an implant 20 to the dilator 30. In some embodiments, the first coupling portion includes a securing mechanism that can be used to tighten a noose around a portion of an implant. In some embodiments, the first coupling portion includes a loop through which an implant can be disposed. In other embodiments, the first coupling portion can include a protective sleeve or sheath. For example, the dilator 30 can include a protective sheath that can be slidably disposed over at least a portion of the elongate body of the dilator. The sheath can function as a protective cover for the implant 20 during implantation as described in more detail below with reference to specific embodiments. In other embodiments, the dilator can include a protective sleeve configured to be coupled to an implant 20. In such an embodiment, after delivery of the implant to the pelvic region, the sleeve can be cut for removal of the dilator 30 from the implant.

The distal end of the dilator 30 can include a second coupling portion (not shown in FIG. 1) configured to releasably couple the dilator 30 to the delivery device 28. The delivery device 28 can have a variety of different configurations and can include different types of coupling portions for coupling the dilator 30 to the delivery device 28. For example, the dilator 30 can include a suture at a distal end, and a trocar needle coupled to the suture. The trocar needle can be used to associate the dilator 30 to a delivery device 28. In other embodiments, the distal end of the dilator 30 includes a loop or other type of connector that can be used to associate the dilator 30 to a delivery device 28.

The dilator 30 can also be color-coded. For example, when an implant having multiple arms or straps is to be delivered to a pelvic region, a separate dilator having a unique color can be associated to each strap of the implant. Such color-coding can help with the organization of the delivery process.

The dilator 30, together with the delivery device 28, can be used to insert and deposit the implant 20 within a pelvic region of a patient. The dilator 30 can be coupled to the implant 20 prior to the dilator 30 being placed within a pelvic region of a patient, or after the dilator 30 has been placed. For example, if the implant 20 includes multiple straps or arms such as with a pelvic floor repair implant, the implant can be associated to the dilator 30 after the dilator 30 has been placed within the pelvic region using a delivery device 28. Placing the dilator 30 into the patient's body prior to attaching the implant to the dilator 30, minimizes handling of the implant and can thus help reduce damage to the implant during delivery. In addition, inserting the dilator 30 into the pelvic region without the implant attached can improve visibility during positioning of the dilator 30.

With the implant 20 coupled to the dilator 30, and the dilator 30 coupled to the delivery device 28, the delivery device 28 can be used to deliver the implant 20 into a pelvic region. Specifically, the dilator 30 can be inserted through a vaginal incision and into the pelvic region using a transvaginal approach using the delivery device 28. As stated above, there are various different types of delivery device 28. For example, some embodiments of a delivery device 28 have an articulating head, others have multiple carrier members, while still others have a re-shapeable shaft. The particular embodiment of a delivery device used can depend on the particular problem being treated and the reachability of the location within the pelvic region.

Having described above various general principles, several exemplary embodiments of these concepts are now described. These embodiments are only examples, and many other configurations of an implant 20, delivery device 28 and dilator device 30 are contemplated, and will be apparent to the artisan in view of the general principles described above and the exemplary embodiments.

Figure 2A:
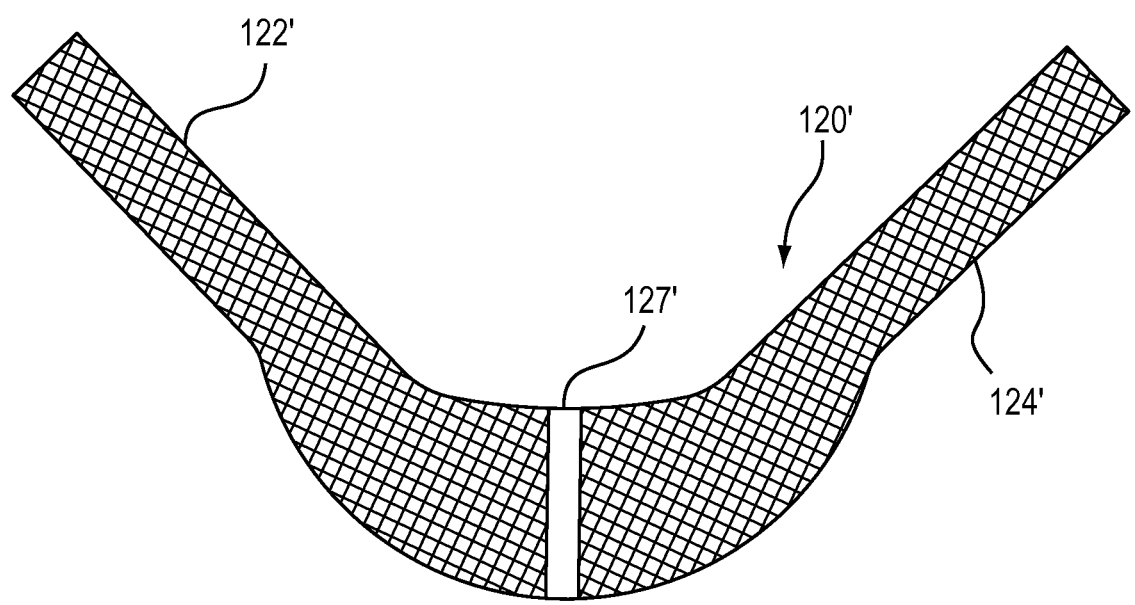

FIG. 2 illustrates an example of an implant that can be delivered to a pelvic region using the devices described herein. The implant 120 includes a first end portion 122, a second end portion 124 and a middle portion 126. In this embodiment, the implant 120 is formed with a mesh material to allow for in-growth of the surrounding tissue when implanted. The first end portion 122 and the second end portion 124 can each have tanged edges (also referred to as tangs) (not shown in FIG. 2), and the middle portion can be untanged. The tanged edges help retain the implant within bodily tissue. The implant 120 also includes a heat seal 132 formed along a longitudinal length of the implant 120. For example, a heat seal can be formed by heating a strand or strands of the mesh material as described above. The implant 120, can be delivered into a pelvic region of a patient using a dilator 130 and a delivery device 128. The implant 120 is just one example of an implant that can be delivered using the dilators and delivery devices described herein, as the devices can be used to delivery a variety of different implants, including implants of different shapes and sizes and implants with multiple arms or straps. FIG. 2A illustrates another example of an implant. An implant 120' includes a first portion 122' and a second end portion 124' that are each angled from a curved and wider middle portion 126'. The implant 120' also illustrates a center or midline mark 127' that can be used by a medical practitioners to help position the implant 120' within a pelvic region.

Figure 3:
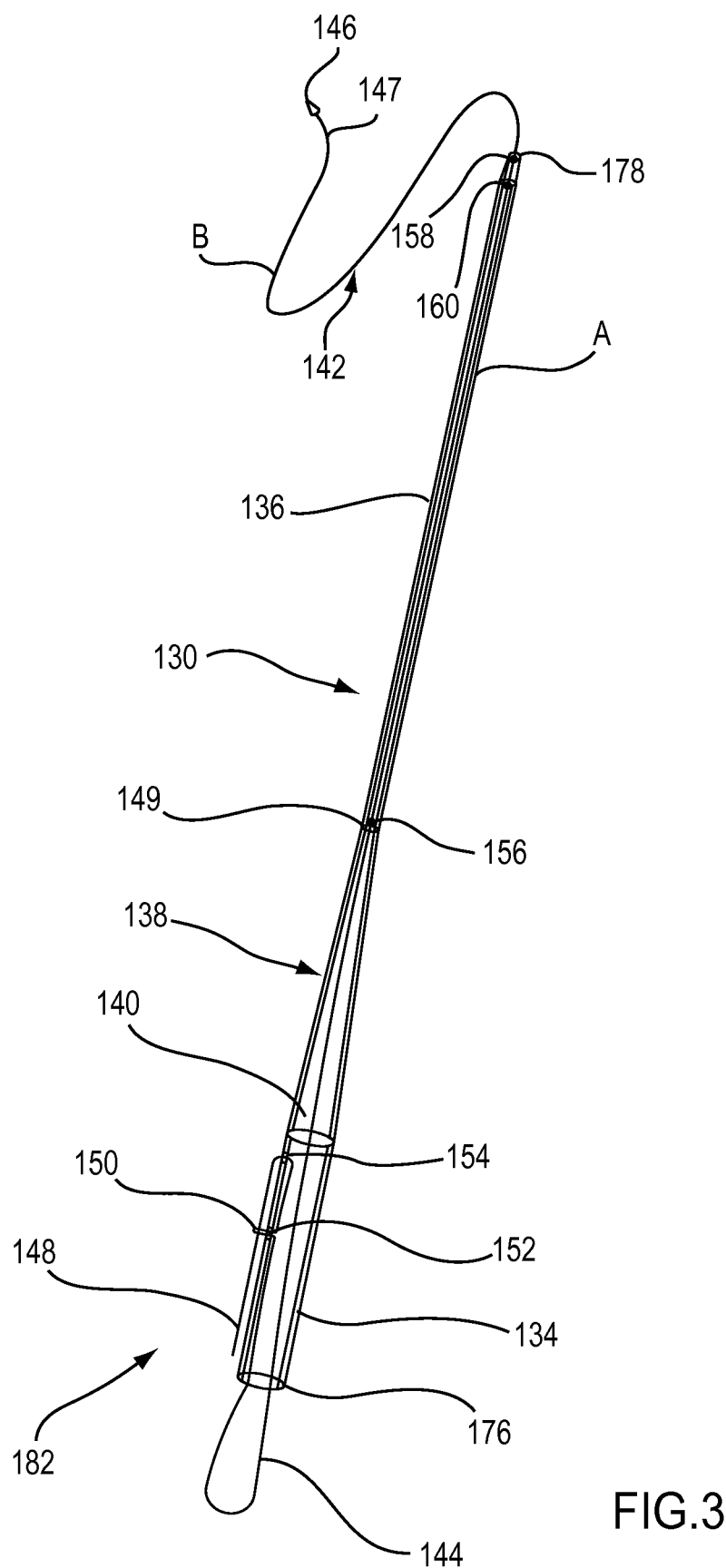
FIG. 3 is a side perspective view of an embodiment of a dilator device.

FIG. 3 illustrates a dilator device 130 according to an embodiment of the invention. The dilator 130 includes an elongate body 138 that defines a lumen 140. The elongate body 138 is shown in see-through form for illustration purposes, but transparency is not necessary. The elongate body 138 is tapered from a proximal end 176 to a distal end 178. Specifically, the elongate body 138 has a first portion 134 and a second portion 136. The first portion 134 of the elongate body 138 has a greater outer diameter than an outer diameter of the second portion 136 of the elongate body 138. In this embodiment, the first portion 134 of the elongate body 138 is tapered from the proximal end 176 of the elongate body 138 to a point 149 between the proximal end 176 and the distal end 178 of the elongate body 138. The second portion 136 of the elongate body 138 is tapered from the point 149 to the distal end 178 of the elongate body 138.

In some embodiments, the first portion 134 of the elongate body 138 can have an inner diameter at the proximal end 176 between, for example, approximately 0.050 inches (1.270 mm) and 0.200 inches (5.080 mm) and a wall thickness, for example, between approximately 0.005 inches (0.127 mm) and 030 inches (0.762 mm). The second portion 136 of the elongate body 138 can be heat formed to the suture 142. Thus, an inner diameter of the second portion 136 can vary depending on the particular suture diameter. In some embodiments, the second portion 136 can have an outer diameter at the distal end 178 between, for example, approximately 0.034 inches (0.864 mm) and 0.045 inches (1.143 mm), and an inner diameter between, for example, approximately 0.020 inches (0.508 mm) and 0.025 inches (0.635 mm). In some embodiments, the second portion 136 of the elongate body 138 can have an outer diameter, for example, of approximately 0.041 inches (1.041 mm) that tapers to an outer diameter of approximately 0.012 inches (0.305 mm) at the distal end 178. In some embodiments, the first portion 134 has an outer diameter at the proximal end 176 of, for example, approximately 0.105 inches (2.667 mm) and a corresponding inner diameter of approximately 0.065 inches (1.651 mm), and the second portion 136 of the elongate body 138 has an outer diameter at the distal end 178 of, for example, approximately 0.034 inches (0.864 mm) and a corresponding inner diameter of approximately 0.020 inches (0.508 mm). In other embodiments, the elongate body 138 is not tapered.

The elongate body 138 can be formed with a material (e.g., a polymer) such that the dilator 130 is flexible and can make a turn, for example, of around 180 degrees when inserted into a patient's body. For example, in one embodiment, the dilator can accommodate a turn radius of 0.236 inches (6 mm) or less.

The dilator 130 also includes a suture 142 that extends through the lumen 140 of the elongate body 138 and forms a noose or loop 144 that extends from the proximal end 176 of the elongate body 138. A trocar needle 146 is coupled to a distal end of the suture 142. The trocar 146 is used to associate the dilator device 130 to the delivery device 128, illustrated in FIG. 7. The portion of the suture 142 that extends from a distal end 178 of the elongate body 138 is also referred to herein as a distal leader or distal leader end. The suture 142 is knotted within the lumen 140 of the elongate body 138 in three locations to secure the suture 142 to the elongate body 138. A first knot 158 and a second knot 160 are each positioned near the distal end 178 of the elongate body 138 to prevent relative movement between the elongate body 138 and the portion of the suture 142 that extends from the distal end 178 and the elongate body 138. The knots 158 and 160 form a friction fit with an inner wall of the elongate body 138. A third knot 156 is positioned within the lumen 140 adjacent the point 149 of the elongate body 138. As with the first and second knots, 158 and 160, the third knot 156 forms a friction fit with the inner wall of the elongate body 138 and helps minimize elongation of the elongate body 138 between the second knot 160 and the third knot 156. For example, in some embodiments, the strength of the suture 142 is such that as the suture 142 is pulled through a tissue within a pelvic region of a patient, the coupling between the elongate body 138 and the suture 142 at knots 158 and 160 could cause the elongate body 138 to stretch. The third knot 156 helps to prevent this stretching. Although three knots are illustrated, a different number of knots can be formed to secure the suture 142 to the elongate body 138, or a different method of securing can be used. For example, the elongate body 138 can be crimped at selected locations to secure the suture 142 at various locations to the elongate body 138.

Figure 4:
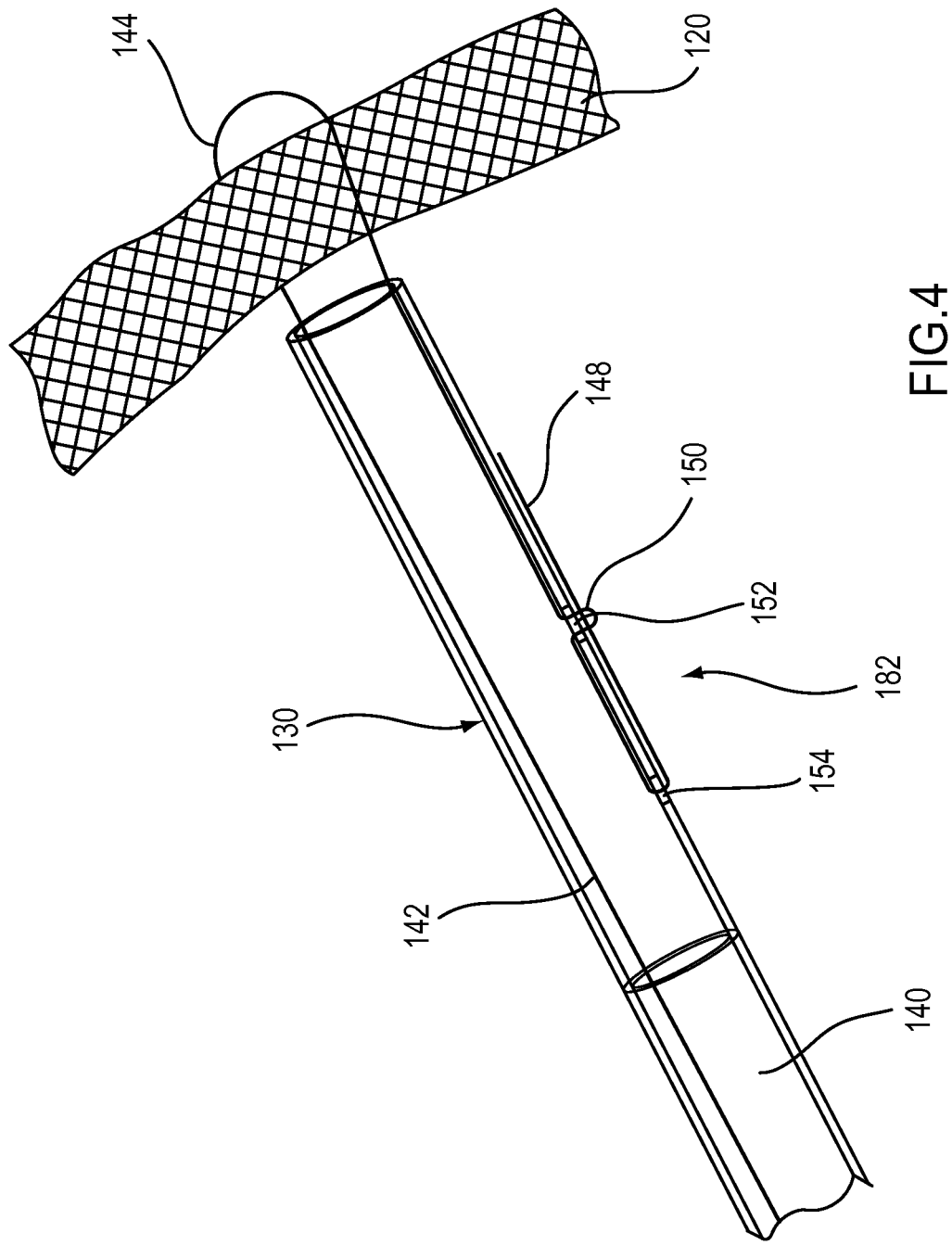
FIGS. 4-6 are side perspective views of a portion of the dilator device of FIG. 3.

The noose 144 is used to releasably couple an implant to the dilator 130. In this embodiment, the suture 142 and the elongate body 138 form a securing mechanism 182 used to tighten the noose 144 around an implant. For example, the securing mechanism can operate similar to a ratchet mechanism. As best shown in FIG. 4, the elongate body 138 defines a first opening 152 and a second opening 154 that extend through a wall of the elongate body 138. A portion of the suture 142 extends through the opening 152 and forms a loop 150. A proximal end portion 148 (also referred to as proximal leader or proximal leader end) of the suture 142 extends through the second opening 154 and passes through the loop 150.

Figure 5:
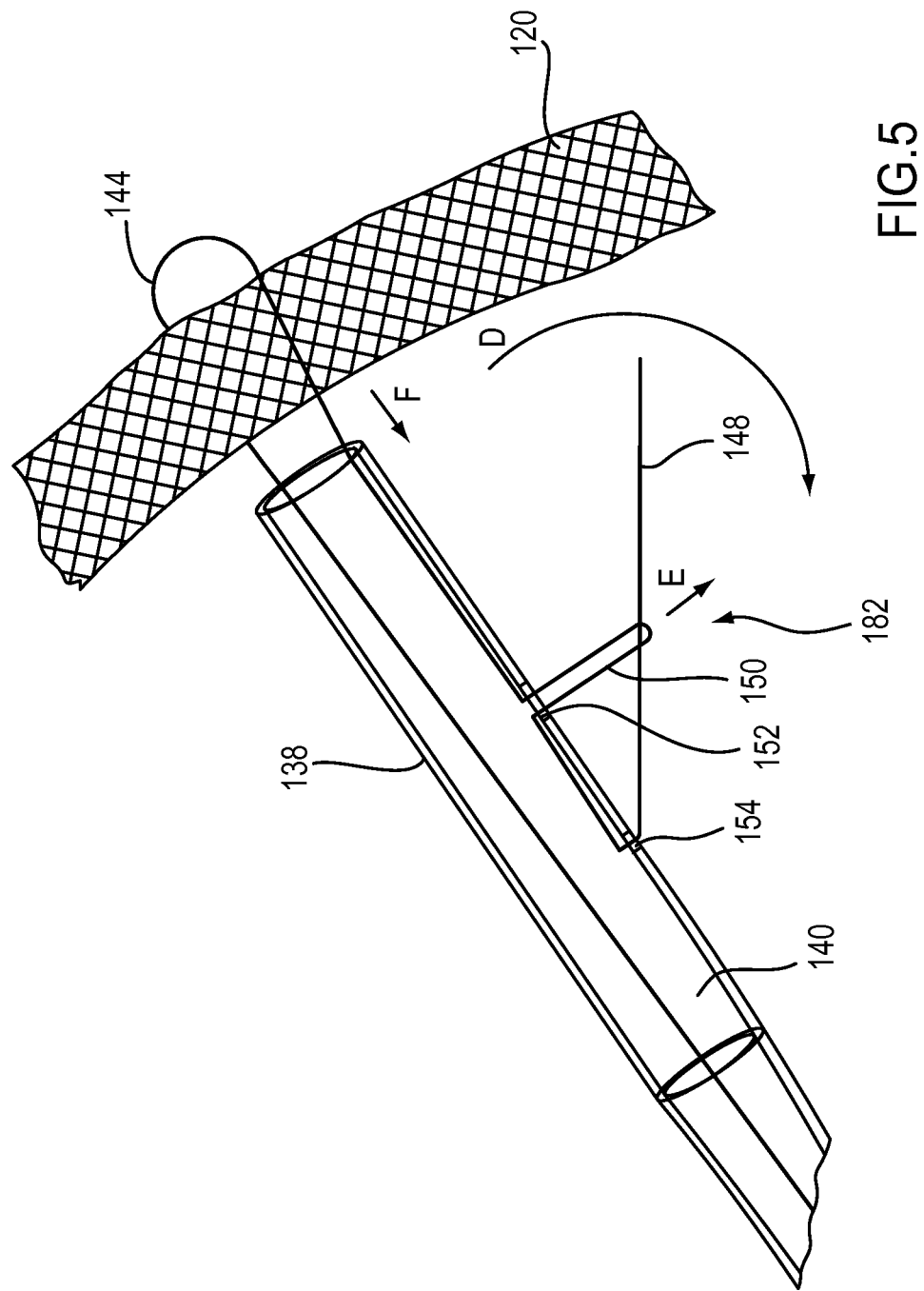
Figure 6:
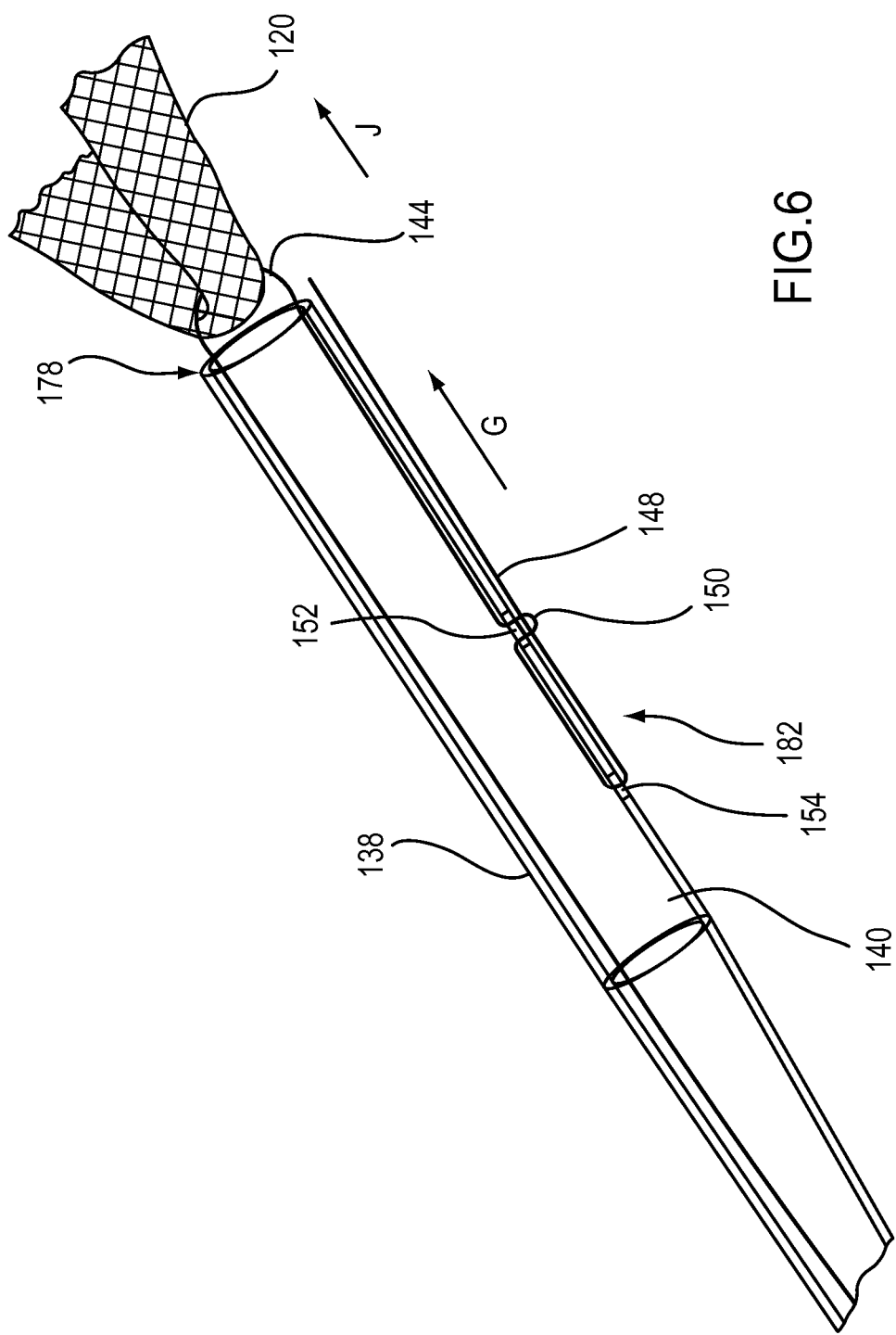

FIGS. 4-6 illustrate the process of coupling an implant, such as implant 120, to the dilator 130. As shown in FIG. 5, the implant 120 is placed or threaded through the noose 144 of the dilator 130 with the proximal leader 148 in a first position that is substantially parallel to adjacent the elongate body 138. The proximal leader 148 of suture 142 is then pulled in a direction of arrow D (shown in FIG. 5) to cause loop 150 to extend in the direction of arrow E. In some embodiments, as the loop 150 extends in length in the direction of arrow E, a length of the noose 144 will be reduced in the direction of arrow F approximately the same length of the extended loop 150. The proximal leader 148 of suture 142 is then pulled in the direction of arrow G, as shown in FIG. 6. This will cause the noose 144 to tighten around the implant 120 and the lassoed portion of the implant 120 will be adjacent to the proximal end 176 of the elongate body 138. The loop 150 will be retracted (e.g., reduced in length); however the loop 150 will be prevented from being pulled through opening 152 because the proximal leader end 148 of the suture 142 extends through the loop 150, and the opening 152 is relatively small. Thus, the size of the noose 144 can be maintained and the noose 144 can be prevented from expanding in the direction of arrow J (FIG. 6). If desired, the proximal leader 148 can be trimmed to shorten its length after securing the implant 120 to the dilator 130. In some embodiments, the securing mechanism 182 is not pulled to tighten the noose, rather, the implant is long enough to prevent the implant from slipping out of the noose 144 when the dilator and implant are pulled through a tissue. The implant 120 can be coupled to the dilator 130 either before or after the dilator 130 is coupled to a delivery device, such as delivery device 128, for implantation.

Figure 7:
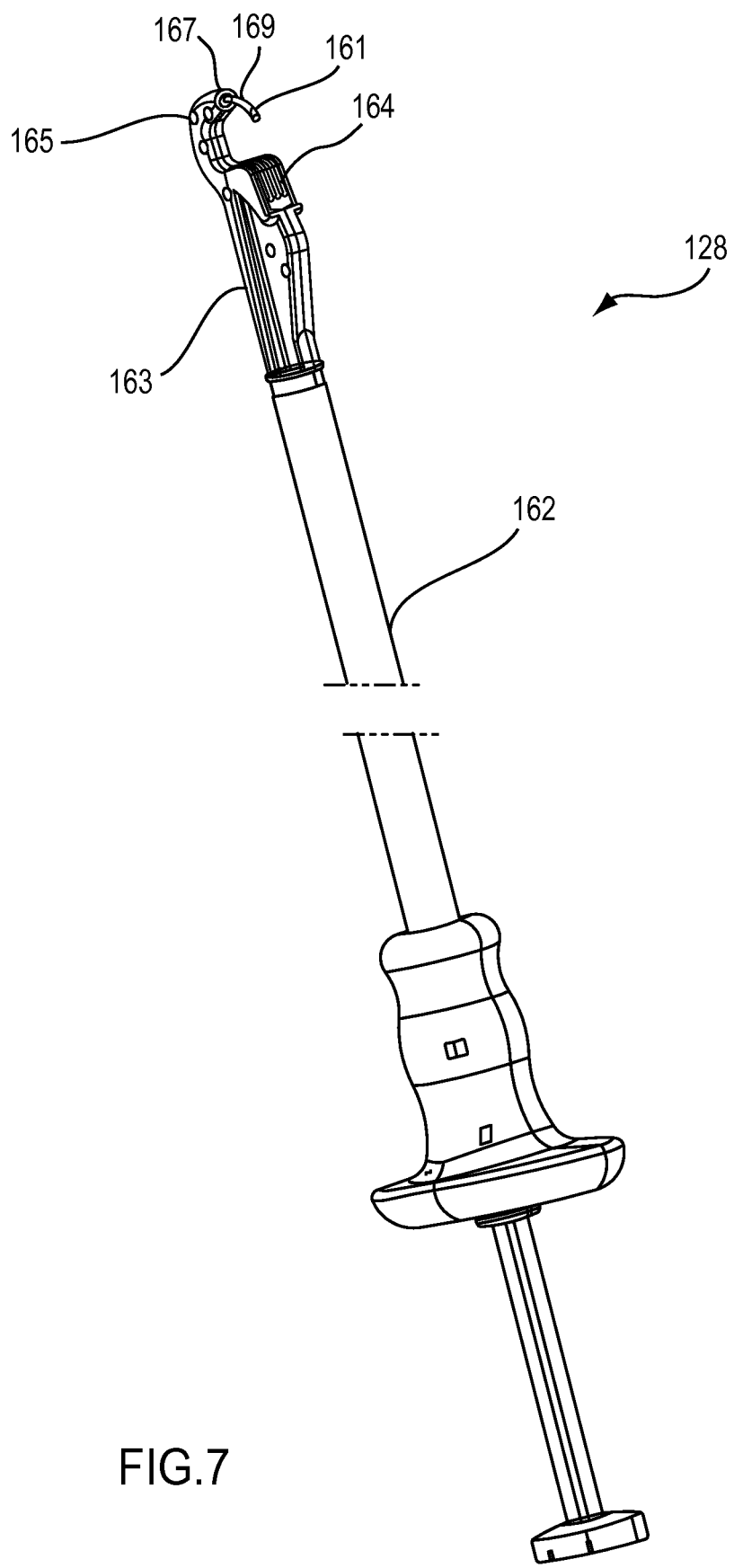
FIG. 7 is a side view of an embodiment of a delivery device.

FIG. 7 illustrates the delivery device 128. The delivery device 128 is a suturing device that can be used to pass an end of a suture or implant through a pelvic tissue. Such a delivery device 128 is also described in U.S. Pat. No. 5,741,277 to Gordon et al. ("the '277 patent"), and U.S. Pat. No. 7,122,039 to Chu ("the '039 patent"), the disclosures of which are hereby incorporated by reference in their entirety. The delivery device 128 includes a shaft body 162, and a distal end portion 163 that includes a carrier member 169 disposed within a curved portion 165 and a catch 164. The curved portion 163 also defines an opening 167 through which the carrier member 169 can exit when the delivery device 128 is actuated. The structure and use of delivery device 128 is described in more detail in the '277 patent and the '039 patent referenced above.

To prepare a patient for deployment of the implant 120 with a delivery device 128, the patient can be given an injection of local anesthesia, for example, along a medial aspect of the obturator foramina and anterior wall of the vagina. An incision is made along an anterior vaginal mucosa. The incision can be, for example, 1.5 to 2.0 cm (0.6 to 0.8 inches) in length and can extend approximately 0.5 cm (0.2 inches) to the meatus. The vaginal epithelium is dissected from the underlying periurethral fascia. The internal edge of an obturator foramen can be identified through palpation, for example at the level of the clitoris.

To deliver the implant 120 to a pelvic region, the trocar 146 of the dilator 130 can be loaded onto the curved distal end 163 of the delivery device 128 (as described, for example, in the '039 patent incorporated herein) such that it is releasably coupled within an opening 161 defined by the carrier member 169. The delivery device 128 can then be used to pass the trocar 146 and the dilator 130 through a pelvic tissue. The dilator 130 can be gripped by the user, for example, at grip point A on the elongate body 138, or at grip point B on suture 142 (as shown in FIG. 3), to help pull the dilator 130 and implant 120 through the desired tissue site. Specifically, the delivery device 128 is actuated or fired such that the carrier member within the curved distal end 163 exits the opening 167 and pushes the trocar 146 through the selected tissue. The trocar 146 is then captured in the catch 164 of the delivery device. A distal end portion 147 (or distal leader) of the suture 142 is then pulled proximally to advance the dilator 130 through the pierced tissue, which in turn pulls the implant 120 through the tissue. For example, with the trocar 146 captured in the catch 164 of the delivery device 128, the delivery device 128 can be pulled proximally.

Figure 8:
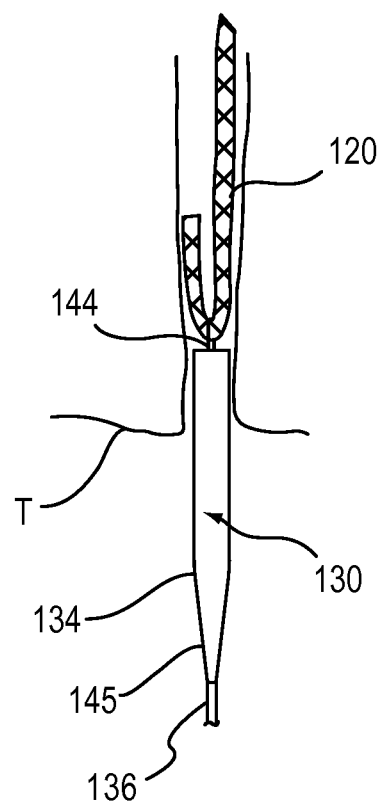
FIG. 8 is a side view of a portion of the dilator of FIG. 3 and an embodiment of an implant shown disposed within a portion of tissue.

After placing the implant 120 through a selected tissue site, the implant 120 can be cut to release the implant 120 from the dilator 130. In some situations, it may be desirable to cut through the elongate body 138 of the dilator 130 at a location, for example, proximal of knot 156. In such a case, the suture 142 disposed within the lumen 140 of the elongate body 138 can also be cut. The physician can then pull an end of the cut suture 142 proximally to release or un-noose the implant 120. FIG. 8 illustrates the dilator 130 leading the implant 120 through a tissue T (e.g., ligament, muscle, soft tissue, etc.). The dilator 130 can be cut, for example, at location 145 through the elongate body 138. The portion of the elongate body remaining partially within the tissue (e.g., after cutting the elongate body 138) can be removed, for example, with forceps or by hand, and the suture 142 can be pulled proximally to release the noose 144 from the implant 120. The implant 120 will be deposited within the tissue T. In the example of FIG. 8, the implant 120 is in a folded configuration, which can minimize the amount of implant material dangling within the pelvic floor region.

Figure 9:
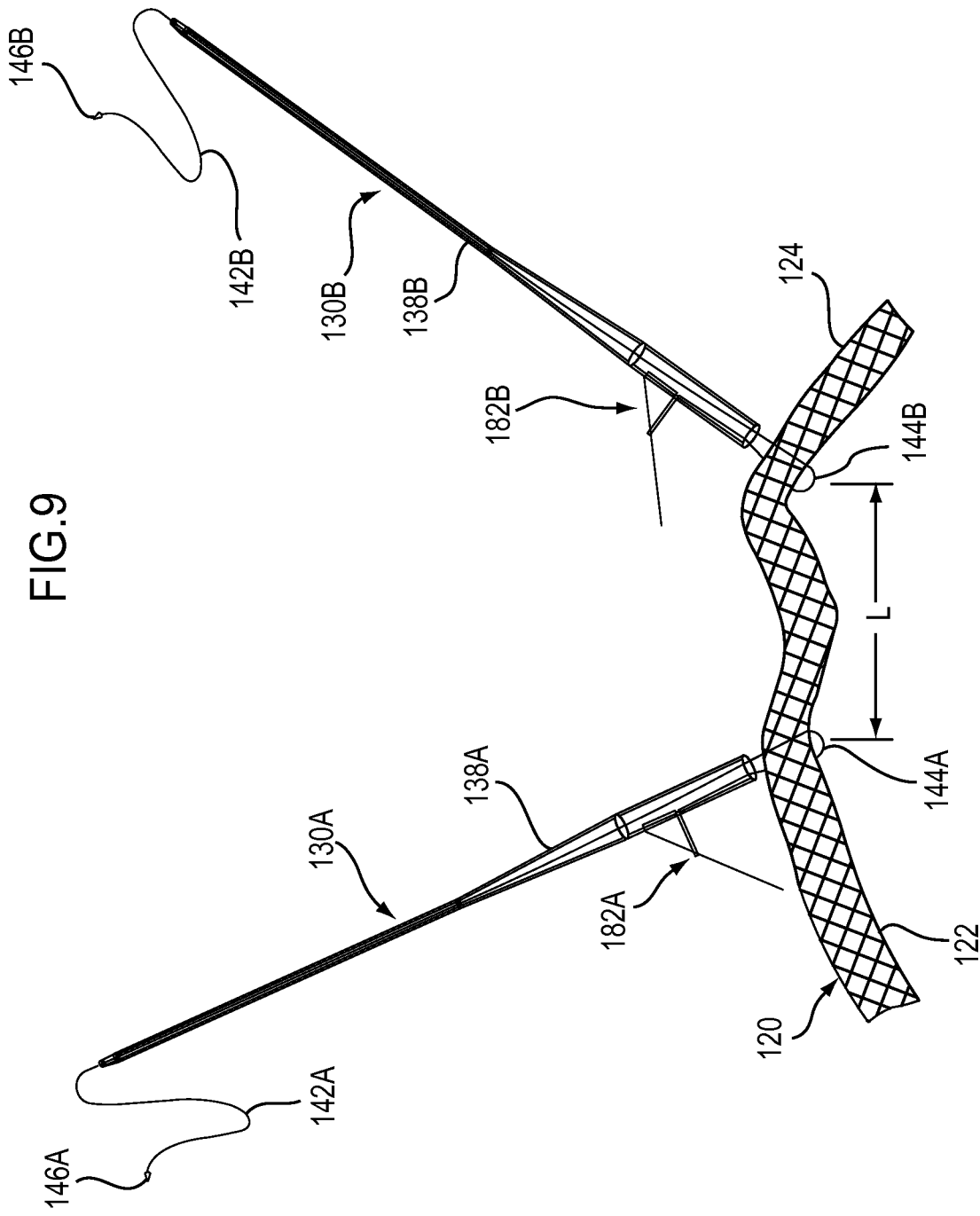
FIG. 9 is a side perspective view of a pair of dilator devices according to an embodiment of the invention and an embodiment of an implant.

In some medical procedures, the use of two dilators may be desired. FIG. 9 illustrates the implant 120 coupled to two dilators 130A and 130B. Each of the dilators 130A and 130B are constructed the same as dilator 130 and function in the same manner. As shown in FIG. 9, the first end portion 122 and the second end portion 124 of the implant 120 are passed through a noose 144A, 144B on dilator 130A and 130B, respectively. The length L illustrates an example length of the middle or support portion 126 of the implant 120. As described above with reference to FIGS. 4-6, securing mechanisms 182A, 182B on the dilators 130A, 130B, respectively, are used to tighten the noose 144A, 144B around the implant 120 and couple the implant 120 to the dilators 130A, 130B. The implant 120 can be secured to dilator 130A and/or dilator 130B either before or after the dilators 130A, 130B have been inserted into the pelvic region. In some embodiments, an implant can be presented to a physician preloaded or coupled to the dilators.

With the dilator 130A loaded onto a delivery device, such as delivery device 128 described previously, the delivery device can be inserted through a vaginal incision. The delivery device can be used to pass a trocar 146A of the dilator device 130A through a first tissue portion within a pelvic region. The dilator 130A can then be pulled through the first tissue portion, along with the attached first end portion 122 of the implant 120 as described above. The same procedure can be performed with dilator 130B on a contra lateral side of the pelvic region to pass the dilator 130B and end portion 124 of the implant 120 through a second tissue portion within the pelvic region. The same delivery device 128 can be used to deliver both the first portion 122 and the second portion 124 of the implant 120 (e.g., sequentially). Alternatively, a different delivery device 128 can be used for delivering each portion of the implant 120, either simultaneously or sequentially.

Figure 10:
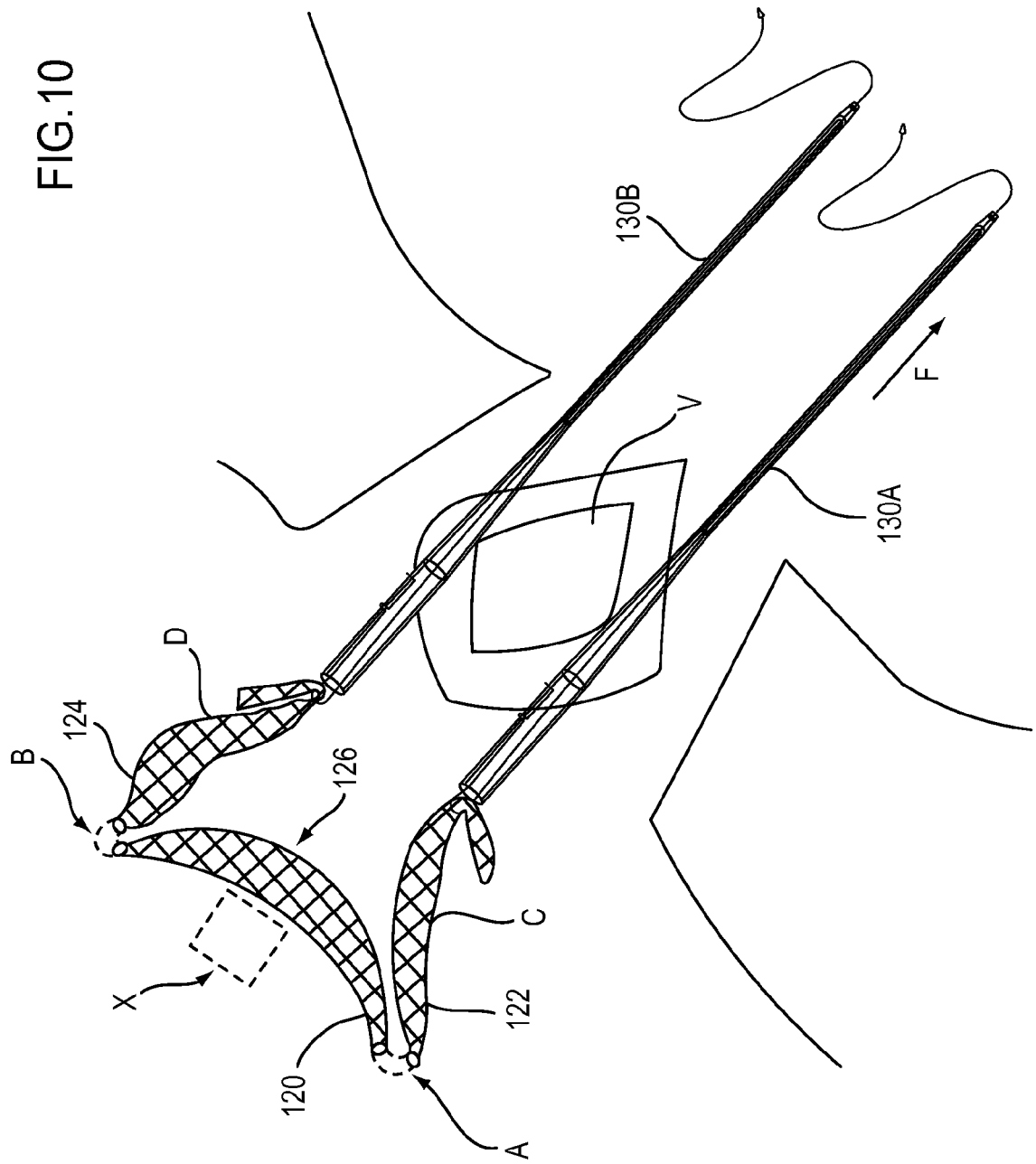
FIG. 10 is a front perspective view of the dilator devices and implant of FIG. 9 shown disposed within a schematic illustration of a portion of a pelvic region.

FIG. 10 illustrates the two dilators 130A and 130B after being passed through tissue locations A and B, respectively, such that the middle or support portion 126 of the implant 120 is disposed beneath an anatomical structure X. FIG. 10 is a schematic illustration of a portion of a pelvic region used here to illustrate the placement of an implant through an incision in a vagina V. Thus, the relative size of the devices and the anatomical structures is not to scale. In some embodiments, the tissue locations A and B are, for example, portions of a sacrospinous ligament or the uterosacral ligament and the structure X is, for example, the uterus, such that the implant is placed for uterine preservation. In another embodiment, the tissue locations A and B are, for example, pubourethral tissue or obturator fossa, and the structure X is a urethra, such that the implant is placed to treat incontinence. In other embodiments, the structure X is a bladder or any other anatomical structure.

After positioning the implant 120, the tension on the implant 120 can be adjusted by pulling the dilators 130A and 130B in the direction of arrow F until the desired tension/support is provided to the structure X. The implant 120 can be trimmed after placement to remove any excess length of the implant 120 and remove the dilators from the patient's body. For example, the implant 120 can be trimmed with scissors at locations C and D shown in FIG. 10. After the dilators 130A and 130B have been decoupled from the implant 120, the tanged end portions of the implant 120 can engage the surrounding tissue at locations A and B to secure the implant 120 in place.

In other embodiments, the implant is placed through the arcus tendineus fascia pelvic for paravaginal repairs including cystoceles, rectoceles and hysteroceles and the structure being supported by the implant is the bladder, rectum, uterus, respectively. For paravaginal repairs, often more than one implant is used to support large areas of the prolapse. Also, although the implant is shown in FIG. 9 as being placed on contra lateral sides of a structure X, the implant can be secured at other fixation points as desired.

Figure 11:
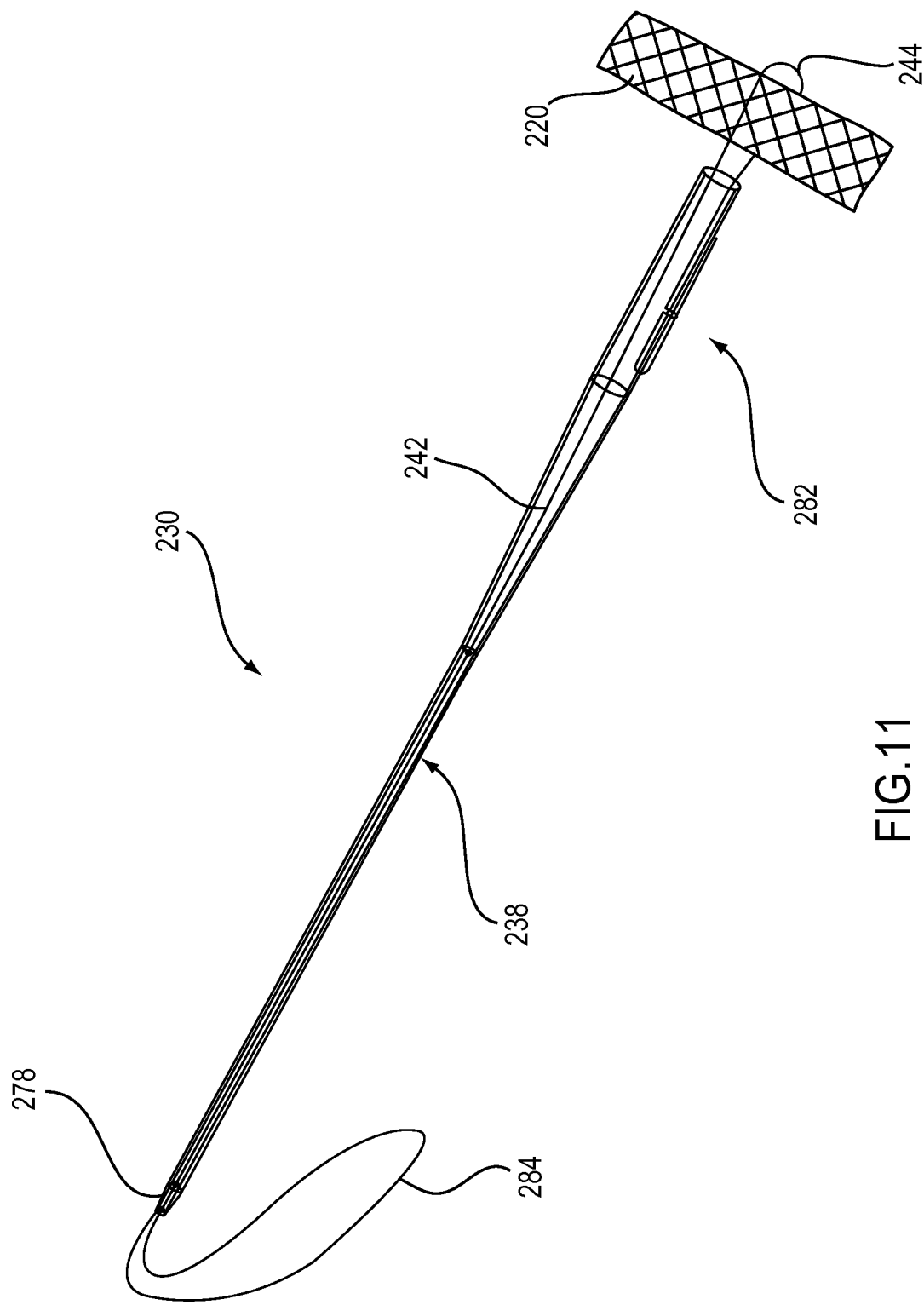
FIG. 11 is a side perspective view of an embodiment of a dilator device.
Figure 12:
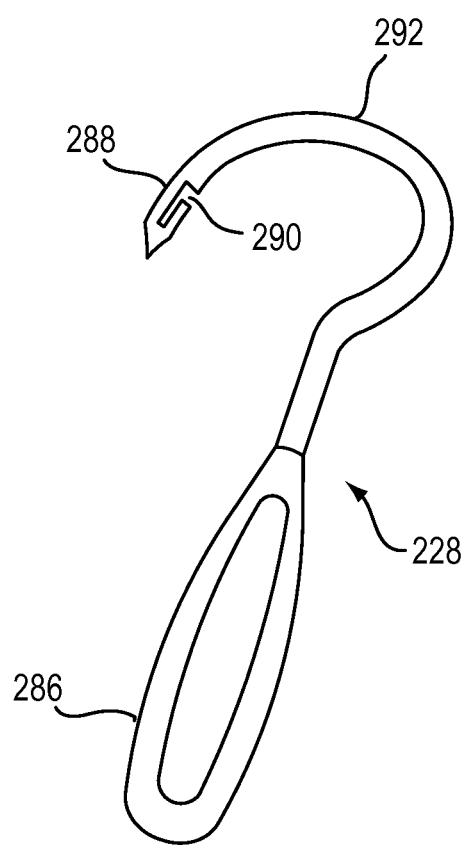
FIG. 12 is a side view of an embodiment of a delivery device.

FIG. 11 illustrates an embodiment of a dilator device configured to be coupled to a different type of delivery device. A dilator device 230 (also referred to as a "dilator") is similarly constructed as dilator 130. The dilator device 230 includes an elongate body 238 and a suture 242 coupled to the elongate body 238. The suture 242 forms a noose 244 disposed at a proximal end portion of the dilator 230. The dilator 230 also includes a securing mechanism 282 as discussed in the previous embodiment, which can be used to tighten the noose 244 around an implant, such as an implant 220. In this embodiment, the suture also forms a connector loop 284 that extends from a distal end 278 of the elongate body 238. The connector loop 284 is used to associate or couple the dilator 230 to a delivery device. For example, the connector loop 284 can be coupled to a delivery device 228 as illustrated in FIG. 12.

The delivery device 228 includes a handle 286, a curved shaft 292, and a connector end 288. The connector end 288 defines a notch 290 that is configured to receive the loop connector 284 of dilator 230. The delivery device 228 can be, for example, an Obtryx Curve device, an Obtryx® Halo device, or a Lynx® device, all manufactured by Boston Scientific Corporation. An example of such a device is also described in U.S. Patent Pub. No. 2005/0075660 and U.S. Patent Pub. No. 2005/0177022, the entire disclosures of which are hereby incorporated by reference in their entirety. Although the delivery device 228 is shown having a curved shaft 292, in other embodiments, the shaft is substantially straight, angled or curved at a different radius of curvature than as shown in FIG. 12. It should be understood that the delivery device 228 is merely an example of the type of delivery device that can be used to deliver the dilator 230 to a desired location within a pelvic region of a patient. The dilator 230 and delivery device 228 can be used, for example, to place anterior straps of a pelvic floor repair implant through an obturator using a retro pubic approach.

FIG. 13 illustrates a dilator device according to another embodiment of the invention. A dilator device 330 (also referred to as "dilator") includes an elongate body 338 and a protective tubular member 366 slidably disposed over a portion of the elongate body 338. The elongate body 338 and tubular member 366 can be formed with a material to allow for bending of the elongate body 338 and tubular member 366 such that the dilator device 330 can bend while being maneuvered through a pelvic region and through tissue. A suture 342 is coupled to a distal end 378 of the elongate body 338 and a trocar 346 is coupled to the suture 342. The suture 342 can be coupled to the elongate body 338, for example, with adhesives, crimping, or other suitable coupling means. In some embodiments, a proximal end of the suture 342 is knotted ant the distal end 378 of the tubular member 366 is molded or formed over the knot of the suture 342 to secure the suture 342 to the tubular member 366. As discussed in detail with respect to the embodiment of FIG. 3, the trocar 346 can be used to associate the dilator 330 to a delivery device, such as delivery device 128.

An implant connector 368 is coupled to a proximal end 376 of the elongate body 338. The implant connector 368 can be, for example, a suture formed in a loop configuration. In other embodiments, the implant connector 368 can be formed with other materials, such as biocompatible plastics, and have other configurations. In alternative embodiments, the elongate body is hollow and the suture extends through an interior lumen of the elongate body. In such an embodiment, the suture can be secured to the elongate body, for example, using knots to form a friction fit between the suture and an interior wall of the elongate body. The suture can also extend from the proximal end of the elongate body to form the implant connector.

Figure 14A:
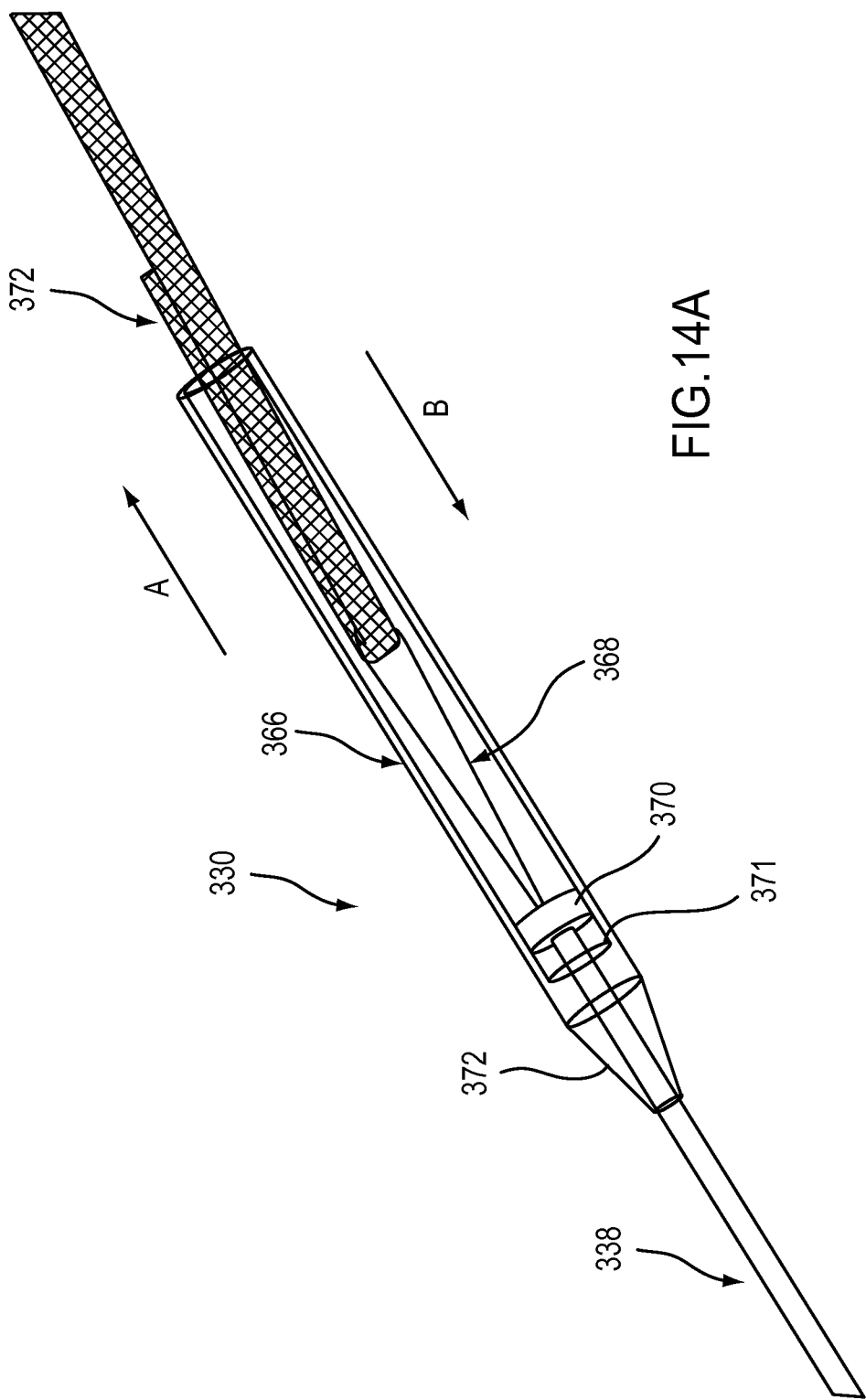
FIG. 14A is an enlarged side view of a portion of the dilator of FIG. 13 and a portion of an implant.

To couple an implant to the dilator 330, a portion of the implant, such as portion 322 shown in FIG. 14A, can be placed through the implant connector 368 similar to placing an implant through a noose as described in the previous embodiments. After the portion 322 has been placed through the implant connector 368, the tubular member 366 can be slidably moved relative to the elongate body 338 in the direction of arrow A such that the tubular member 366 partially covers the portion 322 of an implant. A stop member 370 is disposed at a proximal end 376 of the elongate body 338. The stop member 370 can be monolithically formed with the elongate body 338, or can be a separate component coupled thereto. The tubular member 366 tapers at an end portion 372 and includes a flange 371 molded therein. The flange 371 is configured to engage the stop member 370 to limit the travel of the tubular member 366 as it is moved relative to the elongate body 338 in the direction of arrow A (or to limit the travel of the elongate body 338 when moved relative to the tubular member 366 in the direction of arrow B).

Figure 14B:
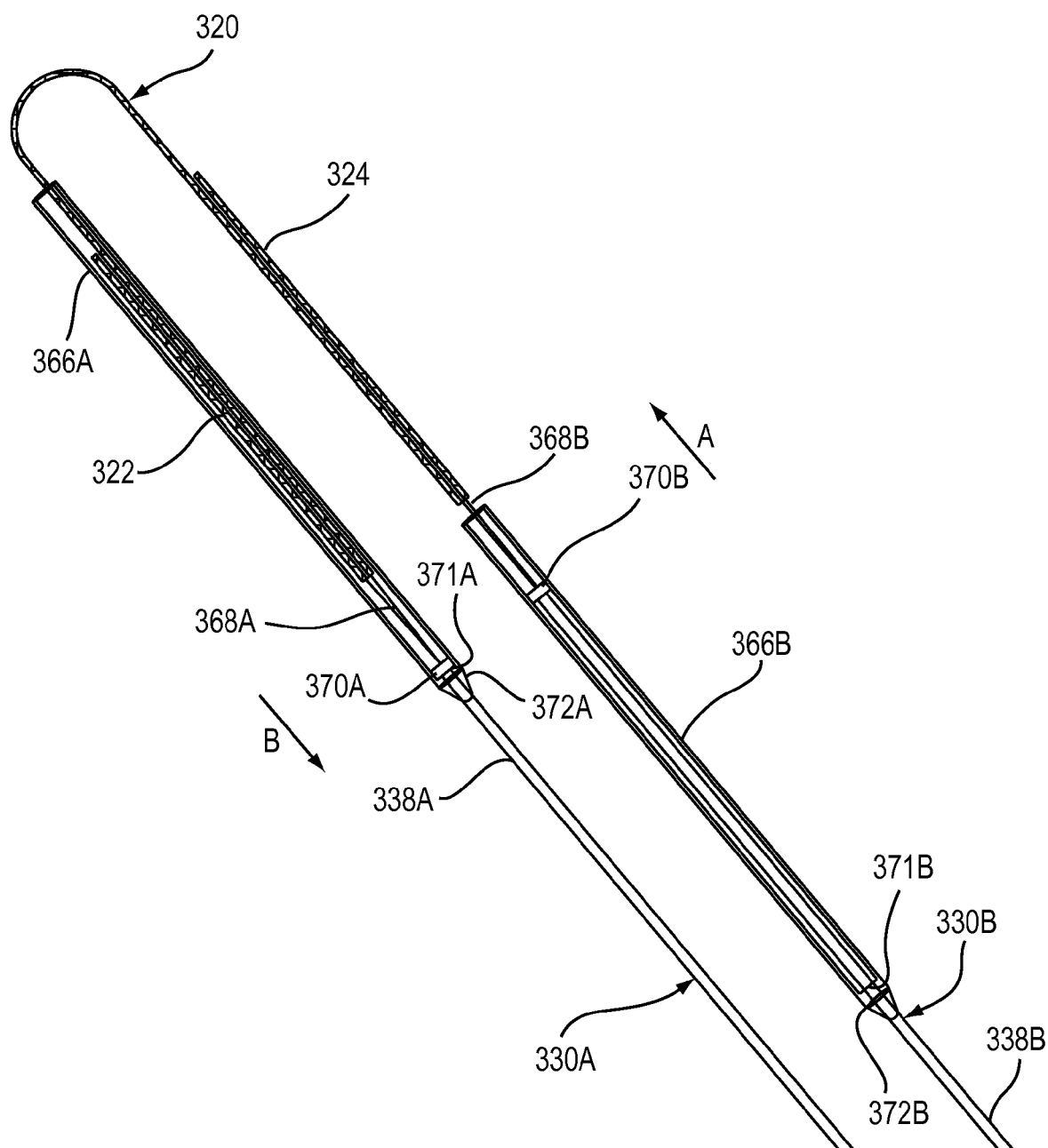
FIG. 14B is a side view of a portion of two dilator devices according to an embodiment of the invention and an embodiment of an implant.

FIG. 14B illustrates the implant 320 coupled to two dilators 330A and 330B. The dilators 330A and 330B are constructed the same as dilator 330 and function in the same manner. The process of securing the implant 320 to the dilator 330A is described, as the process to secure the implant 320 to dilator 330B is identical. To secure the implant 320 to the dilator 330A, a first end portion 322 of the implant 320 is placed through the implant connector 368A and the tubular member 366A is slid proximally relative to the elongate body 338A in the direction of arrow A. This will position the tubular member 366A such that the implant connector 368A and a portion of the implant 320 are disposed within a lumen of the tubular member 366A, as shown in FIG. 14B. The tubular member 366A can help prevent damage to the implant during implantation and premature engagement of the implant with surrounding tissue. The tubular member 366A can also help maintain the implant 320 coupled to the dilator 330A during the insertion of the implant 320. For example, the tubular member 366A can have an inner diameter sized such that it has a frictional fit with at least a portion of the implant 320 to inhibit the implant 320 from dragging out through the looped implant connector 368A.

When the tubular member 366A is moved proximally relative to the elongate body 338A (e.g., in a direction of arrow A), the flange 371A in the tapered end portion 372A of the tubular member 366A will engage the stop member 370A. Thus, the stop member 370A prevents the tubular member 366A from sliding off or being removed from the elongate body 338A when the tubular member 366A is moved in the direction of arrow A and/or the elongate body 338A is advanced in the direction of arrow B.

FIG. 14B also illustrates a second end portion 324 of the implant 320 inserted through the implant connector 368B of the dilator 330B in the same manner. The tubular member 366B of the dilator 330B is not shown disposed over the second end portion 322B, but can be slid in the direction of arrow A to cover the second end portion 324 of the implant 320 in the same manner as described for the dilator 330A.

Figure 15:
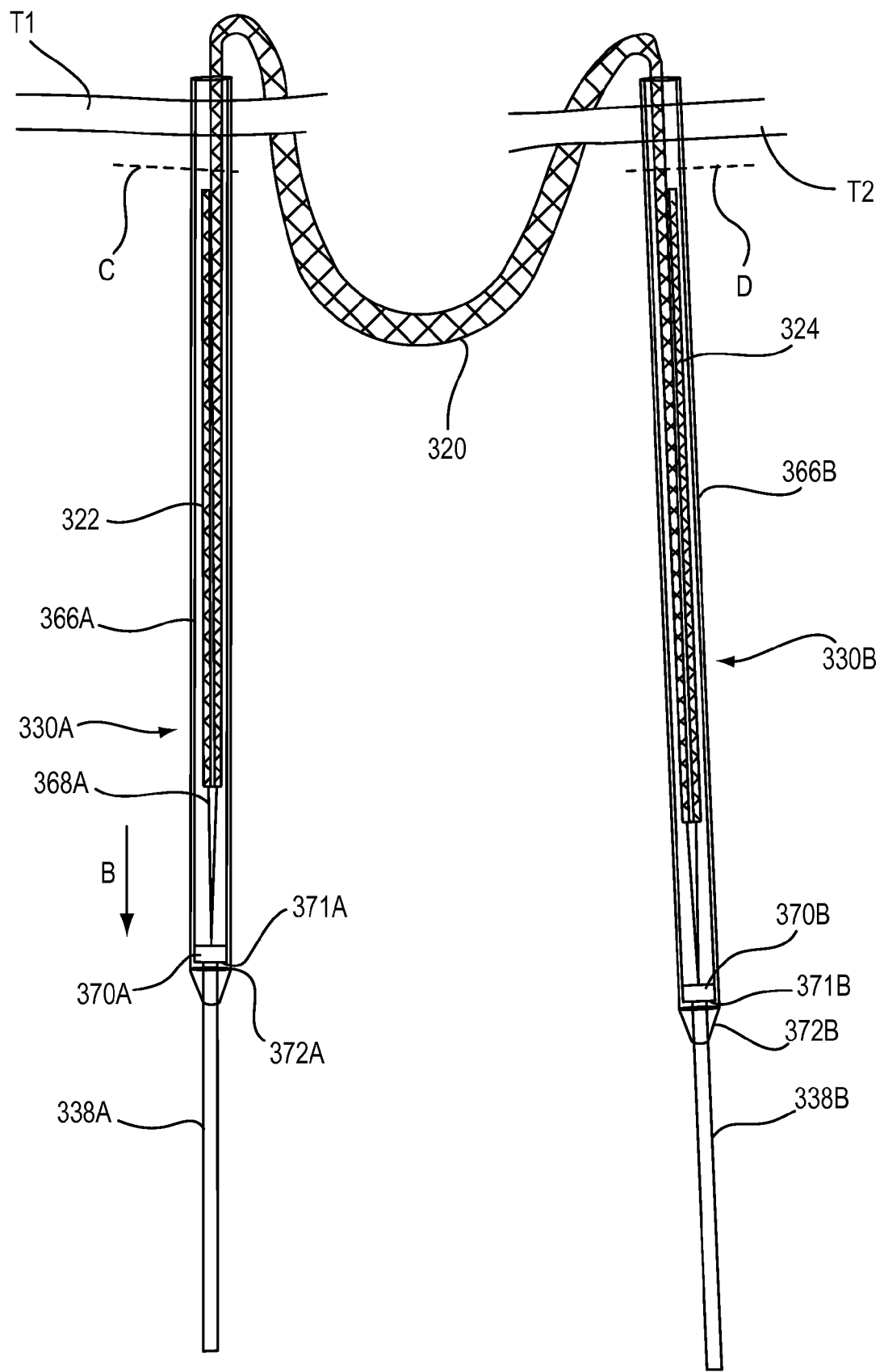
FIG. 15 is a side view of the portion of the two dilator devices and implant of FIG. 14B, shown inserted through tissue and disposed around a schematic illustration of an anatomical structure.

FIG. 15 illustrates a portion of dilator 330A and a portion of dilator 330B each inserted through a schematic representation of pelvic tissue at locations T1 and T2, respectively. The dilators 330A and 330B and implant 320 can be delivered into a pelvic region of a patient in the same manner as the previous embodiment, using, for example, a delivery device 128. For example, the trocar of the dilator 330A (or 330B) can be coupled to the delivery device 128. As with the previous embodiments, the implant 320 can be coupled to the dilators 330A, 330B before or after the dilators have been placed in the pelvic region. For example, the dilator 330A can be inserted into a pelvic region using a delivery device 128 and then an end of the implant 320 can be coupled to the dilator 330A. The other end of the implant 320 can then be coupled to the dilator 330B before or after placement in the pelvic region of the dilator 330B in the pelvic region.

After passing the dilators 330A and 330B through the tissue portions T1 an T2, respectively, as shown in FIG. 15, the elongate bodies 338A and 338B of dilators 330A and 330B, respectively, are pulled or moved in the direction of arrow B, either simultaneously or sequentially. The elongate bodies 338A and 338B can be moved in the direction of arrow B until the stop members 370A, 370B engage the flanges 371A, 371B in the tapered end portions 372A, 372B of the tubular members 366A and 366B, respectively. The implant 320 can be adjusted and tensioned in the same manner as previously described. After tensioning the implant 320, the tubular members 366A, 366B and implant 320 can be cut, for example, using scissors, at locations C and D in FIG. 15. The cut portions of the implant 320 and the cut portions of the dilators 330A and 330B (e.g., the portions of the implant and dilators shown below cut locations C and D in FIG. 15) can then be removed from the patient's body. The remaining portion of the cut tubular members 366A, 366B (e.g., portion of dilators shown above cut locations C and D in FIG. 15) can be removed, for example, by hand, allowing the implant 320 to engage the surrounding tissue at tissue locations T1 and T2. Alternatively, the tubular members 366A and 366B can be moved in the direction of arrow B until the tubular members 366A and 366B are passed completely through the tissue portions T1 and T2 and a portion of the implant 320 is accessible to cut directly. Thus, in this case, only the implant 320 at locations between the tissue portions T1 and T2 and the respective dilator 330A and 330B need to be cut to remove the dilators from the patient's body.

Figure 16:
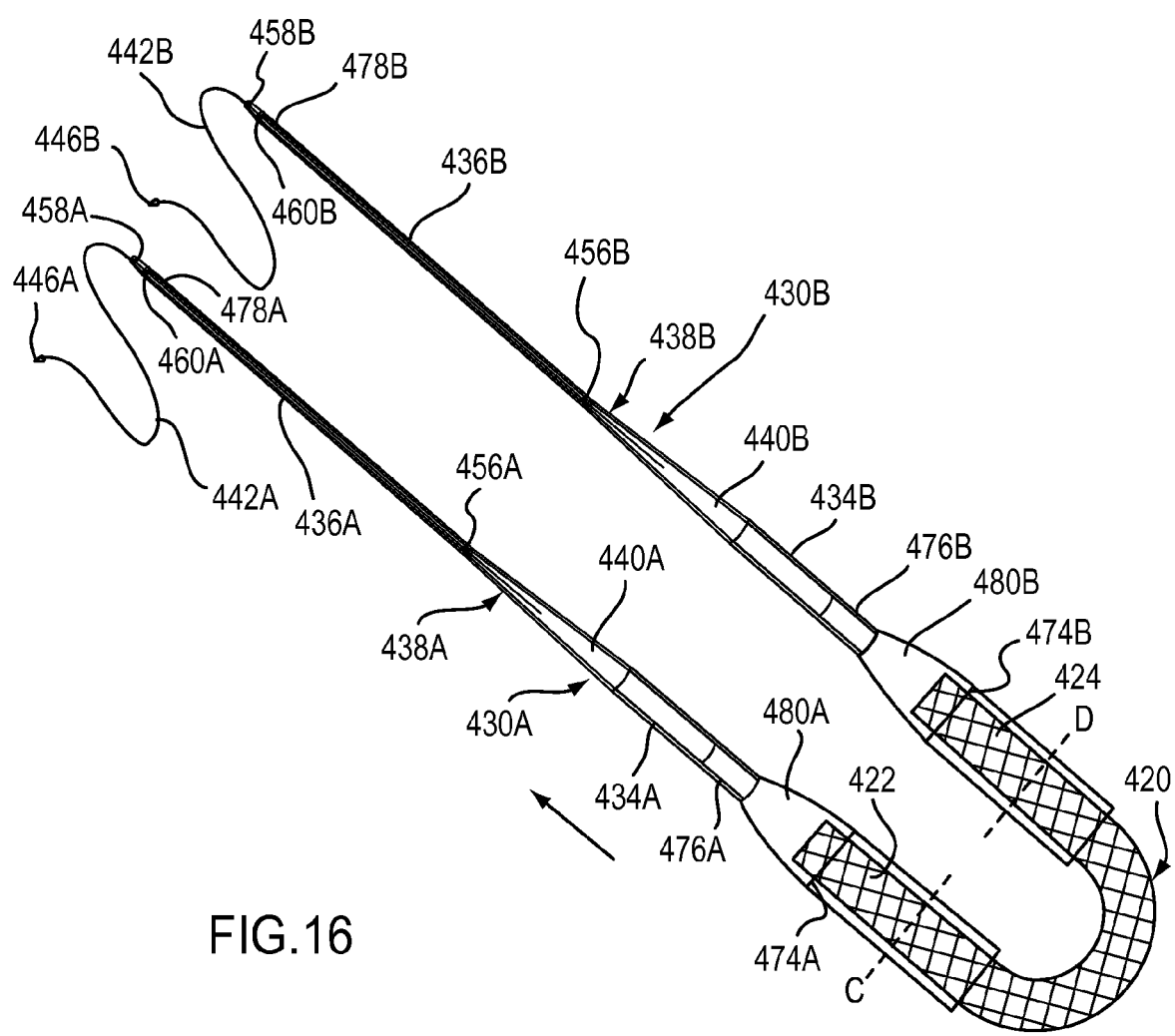
FIG. 16 is a side view of an embodiment of a dilator device.

FIG. 16 illustrates a dilator device according to yet another embodiment of the invention. In this embodiment, an implant is provided pre-assembled to a pair of dilator devices. In other embodiments, an implant is provided pre-assembled to a single dilator device. A pair of dilators 430A and 430B are shown coupled to an implant 420 in FIG. 16. The construction and use of only the dilator 430A is described below, as the construction and use of the dilator 430B is identical.

The dilator 430A includes an elongate body 438A that defines a lumen 440A. Although not necessary, the elongate body 438A is shown in see-through form (e.g., transparent) to illustrate the components disposed within the lumen 440A. A first portion 434A of the elongate body 438A has a greater outer diameter than a second portion 436A of the elongate body 438A. Specifically, the elongate body 438A tapers from a proximal end 476A to a distal end 478A of the elongate body 438A. The dilator 430A also includes a suture 442A that extends through a portion of the lumen 440A of the elongate body 438A. The portion of the suture 442A disposed within the lumen 440A can be knotted to help secure the suture 442A within the lumen 440A. For example a first knot 456A can be formed at approximately a mid-point of the elongate body 438A, and a second knot 458A and a third knot 460A can be formed near the distal end of the elongate body 438A in a similar manner as described for the embodiment of FIG. 3.

A trocar needle 446A is coupled to a distal end of the suture 442A. As with previous embodiments, the trocar 446A is used to associate the dilator device 430A to a delivery device, such as delivery device 128. In other embodiments, the suture 442A can form a loop at the distal end of the elongate body to associate the dilator 430A to a delivery device, such as delivery device 228 shown in FIG. 12. A sleeve 480A is coupled to the proximal end 476A of the elongate body 438A with, for example, heat bonded silicone. Other suitable coupling methods can be used, for example, the sleeve 480A can be heat shrunk onto the elongate body 438A. As shown in FIG. 16 a first end portion 422 of the implant 420 is disposed within the sleeve 480A. A heat seal 474A can be used to secure the first end portion 422 of the implant 420 to the sleeve 480A. In other embodiments, an implant can be coupled to the sleeve 480A using other suitable coupling methods. For example, as shown in FIGS. 27-30 a sleeve can be coupled to an implant using tacks or tacks and a suture. As stated above the dilator device 430B can be coupled to a second end portion 424 of the implant 420 in the same manner.

To deliver the implant 420 to a pelvic region of a patient, the trocars 446A, 446B are each associated to a delivery device, sequentially, or simultaneously, as previously described. Each dilator 430A and 430B can be inserted into a pelvic region and passed through a selected portion of pelvic tissue (not shown) to position a portion of the implant 420 beneath a selected anatomical structure (not shown), such as a urethra or a uterus. After disposing the implant 420 at a selected location within the pelvic region, the sleeves 480A and 480B and the implant 420 can be cut, for example, at locations C and D shown in FIG. 16, such that the implant 420 is cut entirely through, but a portion of the sleeve 480A is still in tack. The cut locations C and D are distal of the heat seals 474A and 474B, to ensure that the sleeves 480A and 480B remain coupled to at least a portion of the end portions 422 and 424 of the implant 420 when the implant 420 is cut. The sleeves 480A and 480B can then be removed from the implant 420 by pulling the dilators 430A and 430B and/or the sleeves 480A and 480B proximally (e.g., in the direction of arrow E). Alternatively, the sleeves 480A, 480B can be cut entirely through, for example, at locations C and D, leaving a portion of the sleeves 480A and 480B surrounding an end of the implant 420 within the patient's body. The remaining portion of sleeves 480A and. 480B can then be removed by hand or with the use of a medical instrument, such as forceps.

Figure 17:
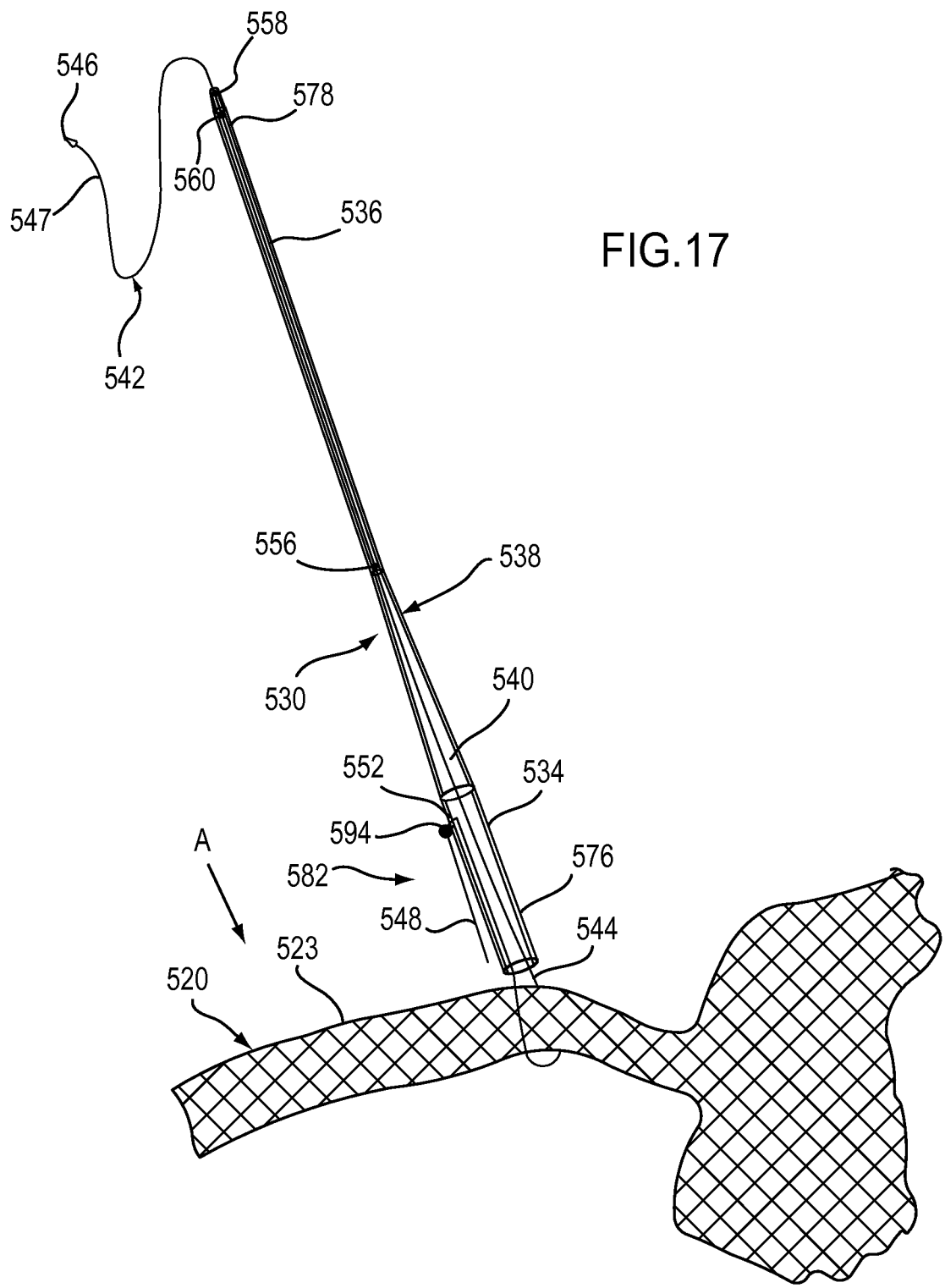
FIG. 17 is a side perspective view of an embodiment of a dilator device.
Figure 18:
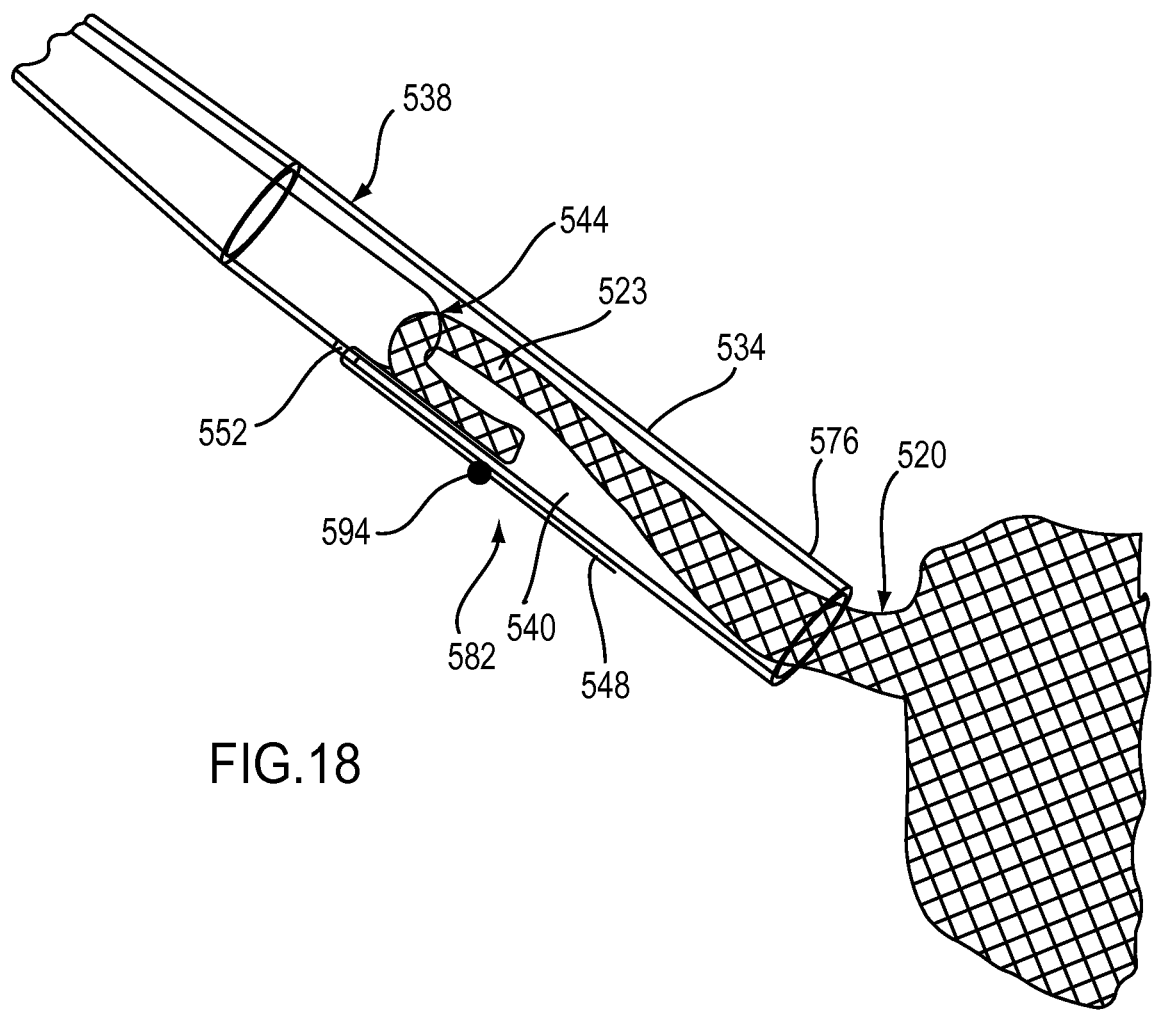
FIG. 18 is a side perspective view of a portion of the dilator device and implant of FIG. 17, shown with the implant partially disposed within a lumen of the dilator device.
Figure 19:
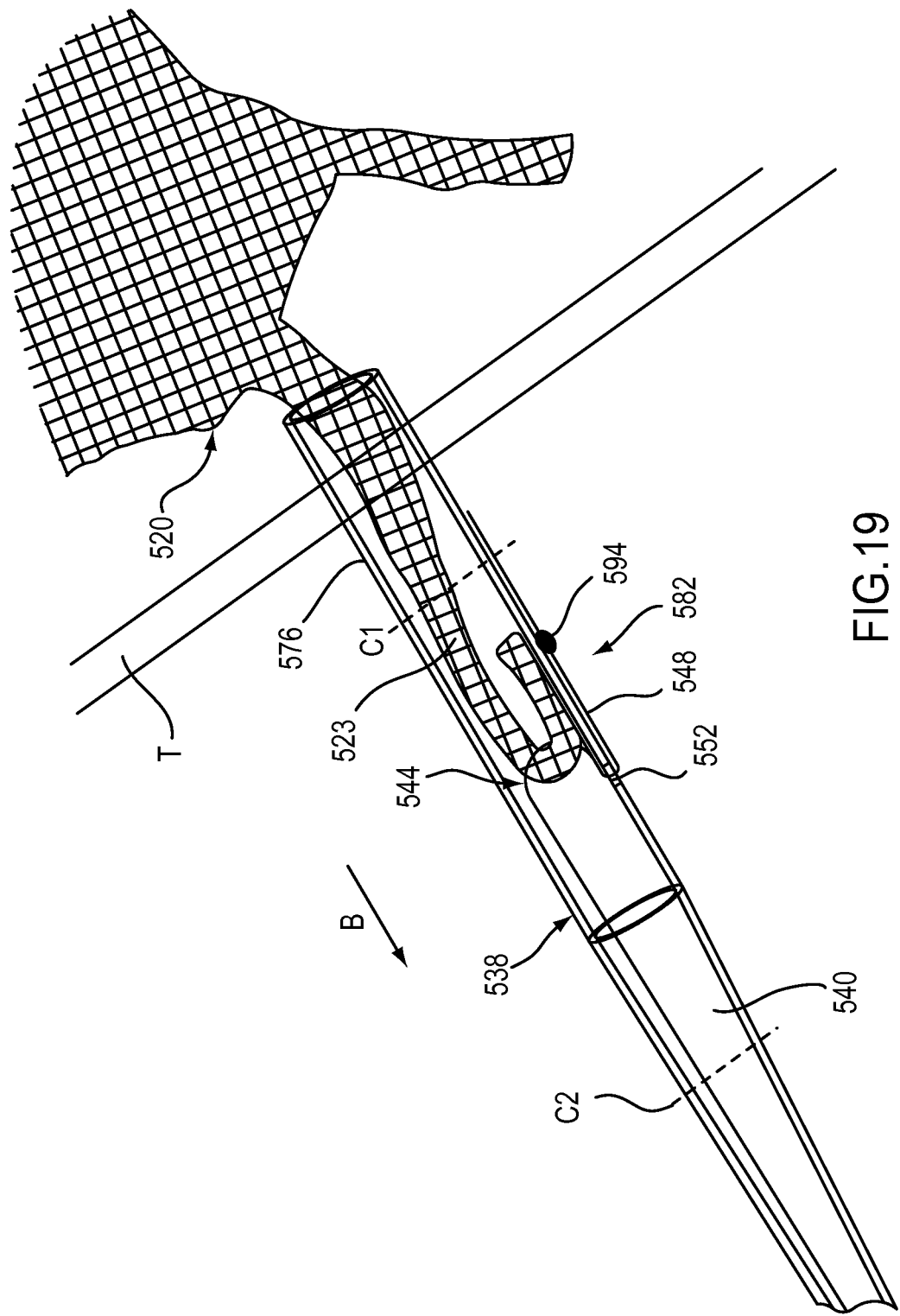
FIG. 19 is a side perspective view of a portion of the dilator device and implant of FIGS. 17 and 18 shown partially pulled through a tissue.

FIGS. 17-19 illustrate another embodiment of a dilator device. A dilator 530 includes an elongate body 538 that defines a lumen 540. The elongate body 538 is tapered from a larger proximal end 576 to a smaller distal end 578. In this embodiment, the elongate body 538 includes a first portion 534 that has a greater outer diameter than an outer diameter of the second portion 536 of the elongate body 538. In other embodiments, the elongate body 538 has the same diameter along an entire length of the elongate body 538.

The elongate body 538 has an outer diameter, and corresponding inner diameter, that is sufficiently large to allow for at least a portion of an implant to be pulled into the lumen 540 of the elongate body 538 as described in more detail below. For example, the elongate body 538 can have an outer diameter at the proximal end 576 of approximately 0.105 inches (2.667 mm) and a corresponding inner diameter of approximately 0.065 inches (1.651 mm). The second portion 536 of the elongate body 538 can have an outer diameter, for example, of approximately 0.041 inches (1.041 mm) that tapers to an outer diameter of approximately 0.012 inches (0.305 mm) at the distal end 578.

The dilator 530 also includes a suture 542 that extends through the lumen 540 of the elongate body 538 and forms a noose 544 that extends from the proximal end 576 of the elongate body 538. A proximal end portion 548 of the suture 542 extends from the noose 544 through a portion of the lumen 540 and exits an opening 552. The suture includes a knot 594 disposed on the proximal end portion 548 of the suture 542 to prevent the proximal end portion 548 from being pulled into the lumen 540, as best shown in FIG. 18. For example, the knot 594 can be sized such that it cannot be pulled through the opening 552. The suture 542 is also knotted within the lumen 540 of the elongate body 538 in three locations to secure the suture 542 to the elongate body 538. For example, the suture 542 includes a first knot 558, a second knot 560, and a third knot 556 as described for the embodiment of FIG. 3. As with the previous embodiment, a different number of knots can be formed to secure the suture 542 to the elongate body 538, or a different method of securing can be used.

A distal end of the suture 542 extends from the distal end 578 of the elongate body 538. A trocar needle 546 is coupled to a distal end 547 of the suture 542. The trocar 546 can be used to associate the dilator device 530 to a delivery device 528, as previously described for other embodiments. In other embodiments, a distal end portion of the suture 542 can form a loop, rather than having an end with a trocar needle, to associate the dilator to a L-notch type delivery device (e.g., delivery device 228).

The noose 544 and proximal end portion 548 form a securing mechanism 582 that is used to tighten the noose 544 around an implant in a similar manner as described for the dilator of FIG. 3. In this embodiment, however, to tighten the noose 544 around an implant, the proximal end portion 548 of the suture 542 is simply pulled in a direction of arrow A shown in FIG. 17. Only a portion of an implant 520 is shown in FIGS. 17-19. The implant 520 is a pelvic floor repair (PFR) implant that has multiple arms. An arm 523 of the implant 520 is placed through the noose 544.

With the arm 523 of the implant 520 placed through the noose 544, the proximal end portion 548 of the suture 542 is pulled in the direction of arrow A, which will pull at least a portion of the arm 523 into the lumen 540 of the elongate body 538, as shown in FIG. 18. As stated above, the lumen 540 of the first end portion 534 of the elongate body 538 is sufficiently sized to allow the arm 523 of the implant 520 to be disposed therein. In some embodiments, the entire implant can be pulled into the lumen 540, and in some embodiments only a portion of the implant is pulled into the lumen 540. Also, other types of implants (e.g., other shapes and/or sizes) can be coupled to the dilator 530 in a similar manner. In some embodiments, the entire strap or arm of an implant is pulled into the lumen 540. For example, the strap can be pulled into the lumen up to the shoulder or point where the strap meets a middle or main portion of the implant. In addition, the same or different dilator can be used on other straps of a multi-strap implant in the same manner.

The portion of the implant 520 disposed in the lumen 540 can depend, for example, on the size and configuration of the implant. The elongate body 538 of the dilator 530 provides a protective compartment to help protect the portion of the implant 520 during the delivery procedure. For example, the elongate body 538 functions as a protective compartment to help prevent tangled portions of the implant from prematurely engaging surrounding tissue while being delivered to a selected tissue site. The protective compartment also allows the tension of the portion of the implant 520 (e.g., the strap) to be adjusted in either direction before being released from the dilator 530 and allowed to engage surrounding tissue.

The dilator 530 can be releasably coupled to a delivery device, such as delivery device 120 previously described. The delivery device 120 can then be used to pass the trocar 546 and distal end of the suture 542 through a selected tissue site in a similar manner as described above for previous embodiments. The implant 520 can be coupled to the dilator 530 either before or after the dilator 530 has been pulled through a selected tissue site. FIG. 19 illustrates the dilator 530 after being pulled through a tissue portion T to deposit the arm 523 within the tissue portion T. Once the implant 520 is correctly positioned, the dilator 530 and arm 523 can be cut to release the implant 520 from the dilator 530 as previously described. For example, the dilator 530 and arm 523 of implant 530 can be cut with scissors or another cutting device at locations C1 or C2 in FIG. 19. The cut portion of the dilator 530 remaining in the tissue can be removed by hand or with the aid of an instrument such as forceps, leaving the arm 523 to engage the surrounding tissue. Alternatively, to remove the dilator 530 from the implant 520, the fourth knot 594 can be cut or removed and the dilator 530 pulled in a direction B. As the dilator 530 is pulled in the direction B, the proximal end portion 548 of the suture 542 will pull through the opening 552 and release the noose 544 from the implant 520.

Figure 20:
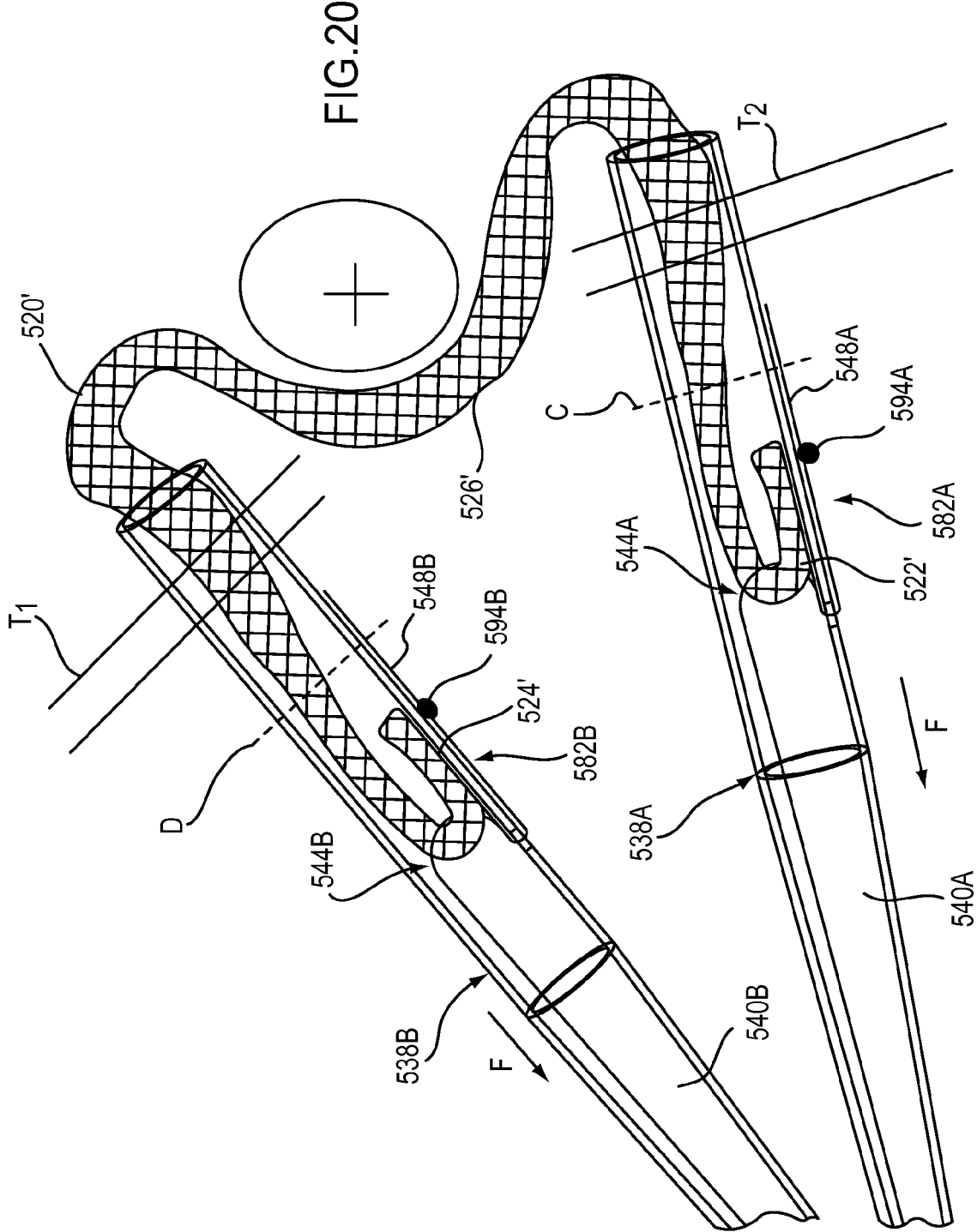
FIG. 20 is a side perspective view of a pair of dilator devices according to an embodiment of the invention and an embodiment of an implant shown being passed through pelvic tissue.

FIG. 20 illustrates a portion of two dilators 530A and 530B, used to place an implant 520' beneath a structure X, such as a uterus or urethra. The dilators 530A and 530B are constructed the same as dilator 530 and can perform the same functions. The dilators 530A and 530 B are each coupled to an end portion of the implant 520'. As shown in FIG. 20, a first end portion 522' of the implant 520' is passed through a noose 544A on the dilator 530A, and a second end portion of the implant 520 is passed through a noose 544B on dilator 530B. Securing mechanisms 582A and 582B of the dilators 530A and 530B, respectively, are used to draw the first end portion 522' and the second end portion 524' into the lumen 540A and 540B, respectively as described above for dilator 530. Also as described previously, sutures 542A and 542B can each include a knot 594A and 594B, respectively, that can prevent the end of the sutures 542A and 542B from being pulled through the openings 522A and 522B, respectively. The implant 520' can be secured to dilator 530A and/or dilator 530B either before or after the dilators 530A and 530B have been inserted into a pelvic region.

A delivery device, such delivery device 128 can be used to deliver the dilators 530A and 530B and the implant 520' as previously described. For example, the dilators 530A, 530B can each be inserted through a vaginal incision and a delivery device 128 can be used to pierce through a selected tissue T1, T2 within the pelvic region. A delivery device 128 can be used to pull each of the dilators 530A, 530B through the tissue T1, T2, respectively, along with the attached implant 520'. FIG. 20 illustrates the two dilators 530A and 530B after being passed through tissue locations T1 and T2, respectively, such that a middle or support portion 526' of the implant 520' is disposed beneath the structure X. In some embodiments, the tissue locations T1 and T2 are, for example, portions of a sacrospinous ligament or the uterosacral ligament, and the structure X is, for example, the uterus, such that the implant is placed for uterine preservation. In another embodiment, the tissue locations T1 and T2 are, for example, pubourethral tissue or obturator fossa, and the structure X is a urethra, such that the implant is placed to treat incontinence.

After positioning the implant 520', the tension on the implant 520' can be adjusted by pulling the dilators 530A and 530B in the direction of arrows F until the desired tension/support is provided to the structure X. The implant 520' and dilators 530A, 530B can be cut, for example, at locations C and D, as indicated in FIG. 20, to release the implant 520' from the dilators 530A, 530B. As with the previous embodiment, cut portions of the dilators 530A and 530B remaining in the patient's body can be removed by hand or with the use of a medical instrument. If the dilators 530A and 530B have been pulled entirely through the tissue portions T1 and T2, then the implant 520' can be cut to remove the dilators 530A and 530B from the patient's body. After the dilators 530A and 530B have been removed from the implant 520', tanged end portions of the implant 520' can engage the surrounding tissue at locations T1 and T2 to secure the implant 520' in place.

FIGS. 21-26 illustrate various securing mechanisms according to other embodiments of the invention. Such securing mechanisms can be included in any of the dilator devices described herein having a securing mechanism. As with previous embodiments, although not required, FIGS. 21-26 illustrate portions of a dilator device in see-through for illustration purposes. An implant can be coupled to the dilator in any of the embodiments described below in a similar manner as described previously. In addition, in any of the embodiments of a dilator described below, the distal end of the dilator can be configured to couple to a delivery device. For example, the distal end of the dilator can include a loop or other connector to associate the dilator to a delivery device such as the delivery device 228. Alternatively, the distal end can include a trocar needle configured to associate the dilator to a delivery device such as delivery device 128.

Figures 21, 22, 23:
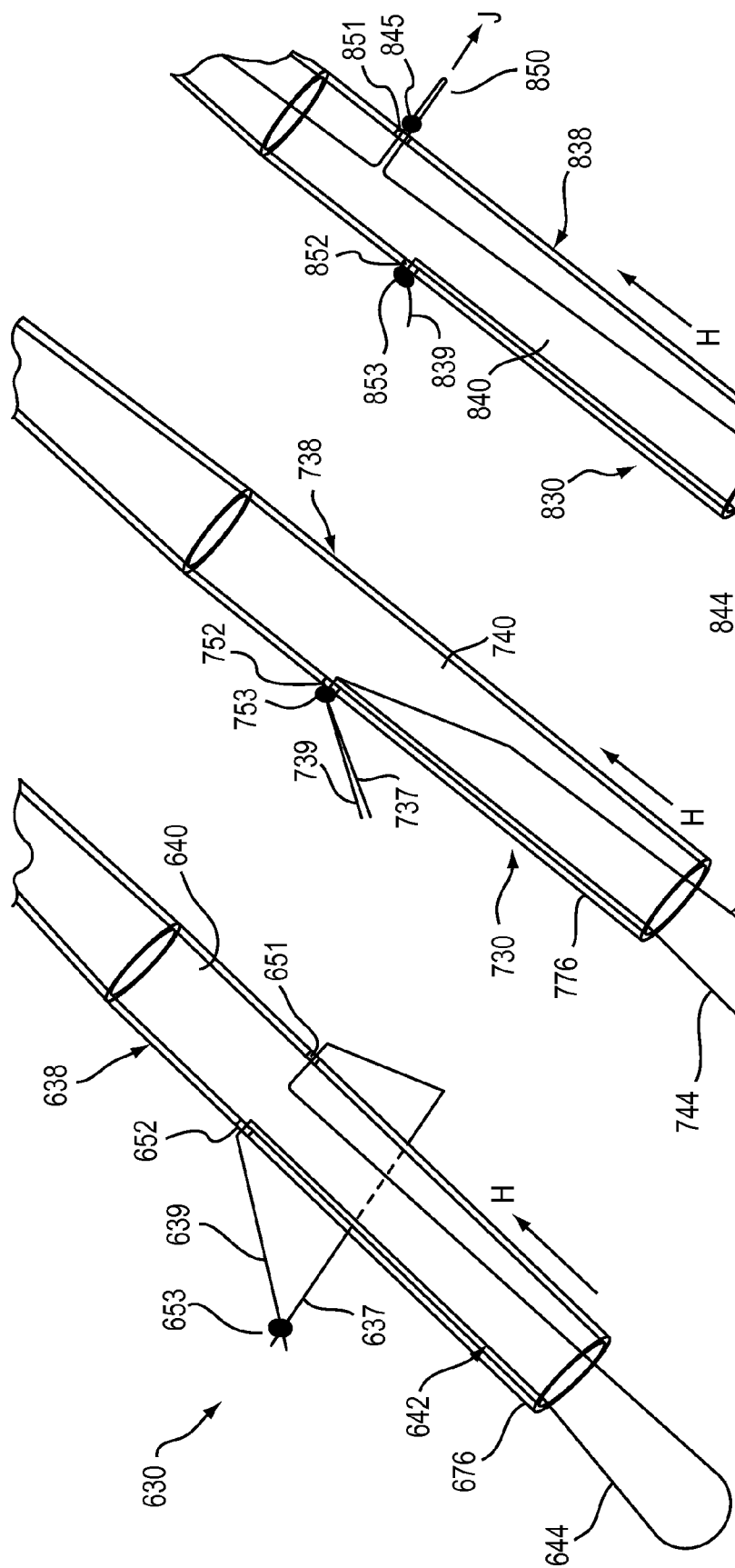

FIG. 21 illustrates a proximal portion of a dilator device 630 having an elongate body 638 that defines a lumen 640, and a suture 642. The suture 642 forms a noose 644 that extends from a proximal end 676 of the elongate body 638. The suture 642 has a first end 639 that extends through an opening 652 defined by the elongate body 638, and a second end 637 that extends through an opening 651 defined by the elongate body 638. The first end 639 and the second end 637 are coupled together with a knot 653, although other coupling methods can alternatively be used. In use, after an implant (not shown) is placed through the noose 644, the two suture ends 637 and 639 are pulled at knot 653 outwardly away from the elongate body 638 such that the noose 644 is drawn into the lumen 640 of the elongate body 638 in a direction of arrow H, and the noose 644 tightens to secure the implant to the dilator 630.

FIG. 22 illustrates a proximal portion of a dilator device 730 having an elongate body 738 that defines a lumen 740, and a suture 742. The suture 742 forms a noose 744 that extends from a proximal end 776 of the elongate body 738. The suture 742 has a first end 739 and a second end 737 that each extend through an opening 752 defined by the elongate body 738. The two ends 739 and 737 of the suture 742 are coupled together with a knot 753, although other coupling methods can alternatively be used. In use, after an implant (not shown) is placed through the noose 744, the two suture ends 739 and 737 are pulled at knot 753 in a direction away from the elongate body 738 such that the noose 744 is drawn into the lumen 740 of the elongate body 738 in a direction of arrow H, and the noose 744 tightens to secure the implant to the dilator 730.

FIG. 23 illustrates a proximal portion of a dilator device 830 having an elongate body 838 that defines a lumen 840, and a suture 842. The suture 842 forms a noose 844 that extends from a proximal end 876 of the elongate body 838. The suture 842 has a first end 839 that extends through an opening 852 defined by the elongate body 838 and is tied in a knot 853 to prevent the first end 839 of the suture 842 from pulling through the opening 852 and into the lumen 840. A portion of the suture 842 is passed through an opening 851 defined by the elongate body 838 and forms a loop 850. A knot 845 is formed to prevent the loop 850 from being pulled through the opening 851 and into the lumen 840. A second end (not shown) of the suture 842 extends to a distal end of the elongate body 838. In use, after an implant (not shown) is placed through the noose 844, the loop 850 is pulled in a direction of arrow J such that the noose 844 is drawn into the lumen 840 of the elongate body 838 in a direction of arrow H, and the noose 844 tightens to secure the implant to the dilator 830.

FIG. 24 illustrates a proximal portion of a dilator device 930 having an elongate body 938 that defines a lumen 940, and a suture 942. The suture 942 forms a noose 944 that extends from a proximal end 976 of the elongate body 938. A portion of the suture 942 is passed through an opening 951 defined by the elongate body 938 and forms a loop 950. A first end 939 and a second end 937 of the suture 942 are passed through an opening 952 defined by the elongate body 938. The two ends 939 and 937 of the suture 942 are tied into a knot 953 or otherwise coupled together. In use, after an implant (not shown) is passed through the noose 944, the loop 950 in a direction of arrow J such that the noose 944 is drawn into the lumen 940 of the elongate body 938 in a direction of arrow H, and the noose 944 tightens to secure the implant to the dilator 930. FIG. 24 illustrates a travel length X of the suture 942 as it is pulled into the lumen 940, which is equal to approximately 2 times the displacement length W of the loop 950. In the embodiment shown in FIG. 24, the length W does not extend the length X or to the proximal end 976 of the elongate body 938. This allows the loop 950 to be clear from tissue as the dilator 930 is pulled through the tissue at about ½ the length of X.

FIG. 25 illustrates a proximal portion of a dilator device 1030 having an elongate body 1038 that defines a lumen 1040, a first suture 1042 and a second suture 1041. A first end 1039 of the suture 1042 and a first end 1035 of the suture 1041 are tied to form a knot 1055 and form a noose 1044 that extends from a proximal end 1076 of the elongate body 1038. A second end 1037 of the suture 1042 and a second end 1033 of the suture 1041 each extend through an opening 1052 defined by the elongate body 1038 and are tied to form a knot 1053. In use, after an implant (not shown) is passed through the noose 1044, the knot 1053 can be pulled outwardly away from the elongate body 1038 such that the noose 1044 is drawn into the lumen 1040 of the elongate body 1038 in a direction of arrow H, and the noose 1044 tightens to secure the implant to the dilator 1030. FIG. 25 shows a proximal end of the sutures 1042 and 1041 extending from knot 1055 has a length P that extends from the noose 1044. The proximal ends (e.g., length P) of sutures 1042 and 1041 can be used for retrieving the noose 1044 if it is inadvertently lodged into the lumen 1040.

FIG. 26 illustrates a proximal portion of a dilator device 1130 having an elongate body 1138 that defines a lumen 1140, and a suture 1142. A first end 1139 of the suture 1142 extends through an opening 1152 defined by the elongate body 1138. A second end 1137 of the suture 1142 extends from a proximal end 1176 of the elongate body 1138 and is tied to form a knot 1155, which forms a noose 1144. The second end 1137 then extends along an outer wall of the elongate body 1138 and is coupled to the first end 1139 with a knot 1153. The suture 1142 in this embodiment has a pulley configuration. In use, after an implant (not shown) is passed through the noose 1144, the knot 1153 is pulled in a direction of arrow A to draw the noose 1144 into the lumen 1140. To move the noose 1144 out of the lumen 1140, the knot 1153 is pulled in a direction of arrow B. The length X illustrates the length of travel of the noose 1144.

FIGS. 27-30 illustrate another embodiment where an implant can be pre-assembled to a pair of dilators, for example, as provided directly from a manufacturer or distributor. A pair of dilators 1230A and 1230B are shown coupled to an implant 1220 via a pair of sleeves 1280A and 1280B. The construction and use of only the dilator 1230A and sleeve 1280A is described below, as the construction and use of the dilator 1230B and sleeve 1280B are identical.

Figure 30:
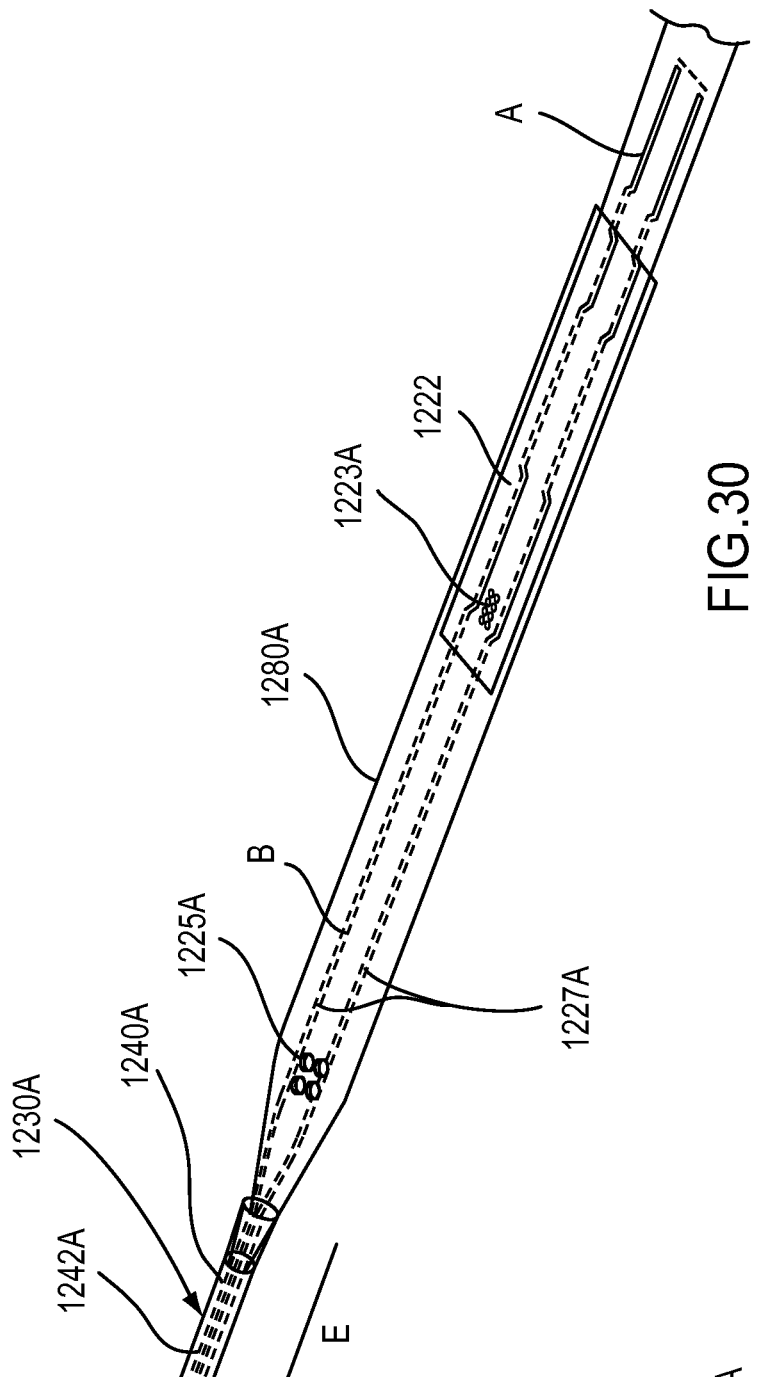
FIG. 30 is an enlarged view of the portion labeled B in FIG. 28.

The dilator 1230A defines a lumen 1240A shown in FIG. 30. Although not necessary, the dilator 1230A is shown in see-through form (e.g., transparent) in FIG. 30 to illustrate the interior of the dilator 1230A. The dilator 1230A tapers from a first portion 1234A to a second portion 1236A. Specifically, the dilator 1230A tapers from a proximal end 1276A to a distal end 1278A. The dilator 1230A can be coupled to the sleeve 1280A, for example, by crimping, heat sealing, stitching, stretching, tip tipping, etc. Alternatively, the sleeve 1280A can be formed to include a portion that forms a tapered dilator (e.g., the dilator and sleeve can be formed monolithically). The dilator 1280A can be used to expand or enlarge a passage during insertion through a tissue, to ease the transition to a cross-section or size of the sleeve 1280A. The sleeve 1280A is also tapered, which also helps provide a lead-in through the tissue.

The sleeve 1280A is secured to the first portion 1222 of the implant 1220 with a suture 1242A. As shown in FIG. 30, the suture 1242A is looped within the sleeve 1280A and weaved or threaded through the implant 1220 at location A. The suture 1242A can alternatively be coupled to the first portion 1222 of the implant 1220 using any of the methods described above for the dilator to sleeve coupling, for example, by crimping, heat sealing, stitching, stretching, tip tipping, etc. In some embodiments, a suture can be threaded to or secured to a strap, for example by knotting. The strands of the suture 1242A forming the loop through the sleeves 1280A (shown in FIG. 30) extend through an interior of the dilator 1230A and can be crimped closed and heat bonded to an interior wall of the dilator 1230A (not shown) to maintain the first portion 1222 within the sleeve 1280A.

Figure 29:
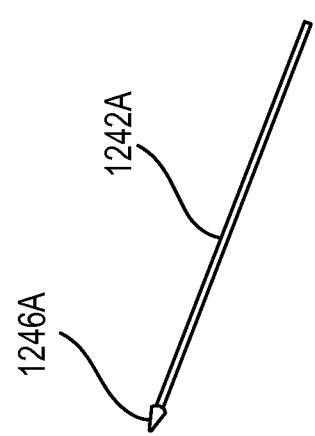
FIG. 29 is an enlarged view of the portion labeled A in FIG. 28.

A leader suture portion of the suture 1242A is coupled to and extends distally from the dilator 1230A. Alternatively, a separate leader suture (separate from the suture 1242A) can be used. A trocar needle 1246A is coupled to a distal end of the leader suture portion 1242A as shown in FIG. 29. As described previously, the trocar needle 1246A can be used to associate the dilator 1230A and implant 1220 to a delivery device, such as a delivery device 128 described above. In other embodiments, the suture portion 1242A can form a loop at the distal end of the elongate body to associate the dilator 1230A to a delivery device, such as delivery device 228 shown in FIG. 12.

In this embodiment, a set of tacks 1225A (four tacks 1225A are shown, but other quantities can be used) are disposed between two strands 1227A of the looped suture 1242A and near a distal end of the sleeve 1280A. The set of tacks 1225A couple a top wall and a bottom wall of the sleeve 1280A together, and maintain separation of the strands of the looped suture 1242A within the sleeve 1280A. A second set of tacks 1223A can be used to lightly secure the first end portion 1222 of the implant 12220 to the sleeve 1280A. The separation of the strands of the suture 1242A enables or helps facilitate a cut to be made through a portion of the sleeve 1280A and only a single strand 1227A of the looped suture 1242A at, for example, location B, to remove the sleeve 1280A from the implant 1220 after being implanted within a pelvic region. Using a set or group of small tacks (rather than a single large tack) can help maintain flexibility of the implant 1220 during delivery into a pelvic region where it may need to fold or bend during insertion. As stated above the dilator 1230B and sleeve 1280B can be coupled to the second end portion 1224 of the implant 1220 in the same manner.

The implant 1220 can be delivered to a pelvic region of a patient, the trocars 1246A and 1246B are each associated to a delivery device (such as delivery device 128), sequentially, or simultaneously, as previously described. Each dilator 1230A and 1230B can be inserted into a pelvic region and passed through a selected portion of pelvic tissue (not shown) to position a portion of the implant 1220 beneath a selected anatomical structure (not shown), such as a urethra or a uterus. After disposing the implant 1220 at a selected location within the pelvic region, the sleeves 1280A and 1280B and the sutures 1242A and 1242B can be cut, for example, at locations C and D shown in FIG. 28, such that a portion of the sleeves 1280A and 1280B are still in tack. The sleeves 1280A and 1280B can then be removed from the implant 1220 by pulling the dilators 1230A and 1230B and/or the sleeves 1280A and 1280B proximally (e.g., in the direction of arrow E in FIG. 30).

Figure 31:
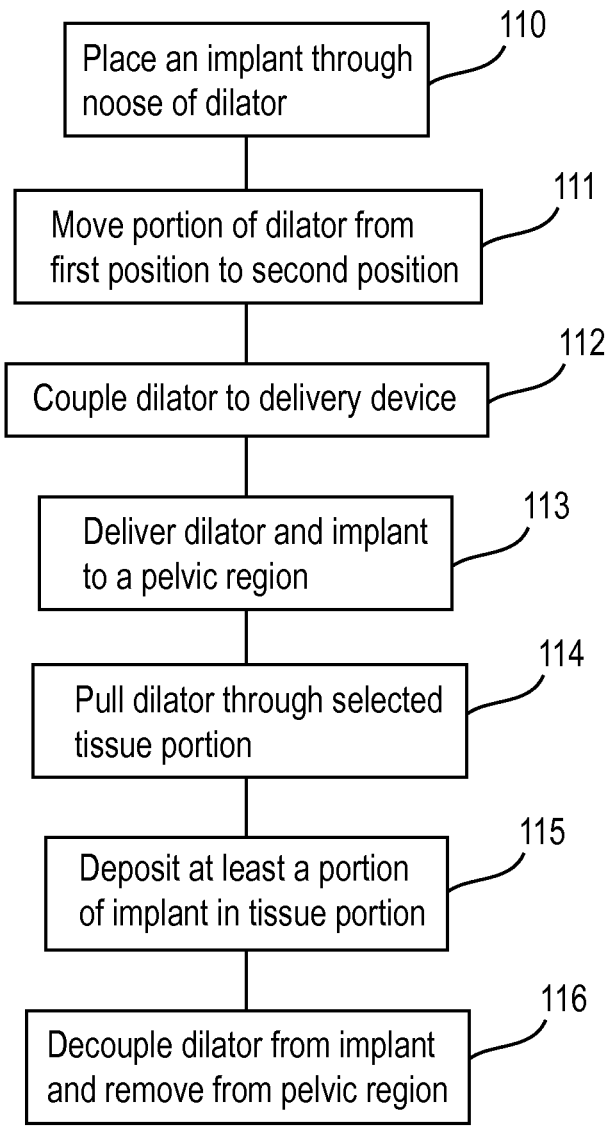
FIGS. 31-33 are each a flowchart of a method according to a different embodiment of the invention.

FIG. 31 is a flowchart of a method according to an embodiment of the invention. At 110, an implant is placed through a noose of a dilator device. At 111, a portion of the dilator is moved from a first position to a second position. In the first position, the portion of the dilator is not covering the implant. In the second position, the portion of the dilator covers at least a portion of the implant. For example, the portion of the dilator can be a tubular member configured to slidably move relative to an elongate body of the dilator between a first position in which the tubular member is not covering a portion of an implant, and a second position in which the tubular member is covering at least a portion of the implant. At 112, the dilator is coupled to a delivery device. At 113, the dilator and attached implant are delivered to a pelvic region of a patient. At 114, the dilator is pulled through a selected tissue portion in the pelvic region. The tissue portion can be, for example a ligament, a muscle, pelvic fascia, soft tissue, etc. At 115, at least a portion of the implant is deposited within the selected tissue portion. At 116 the dilator is decoupled from at least a portion of the implant and removed from the patient's body.

Figure 32:
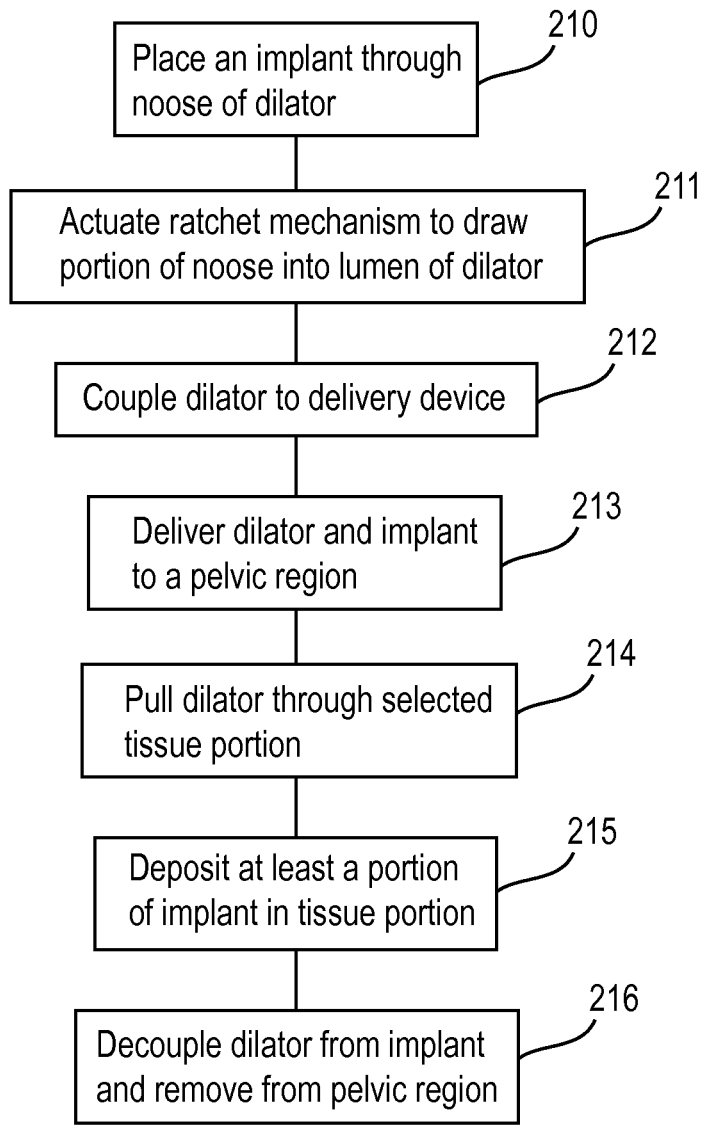

FIG. 32 is a flowchart of another method of the invention. At 210, an implant is placed through a noose of a dilator device. At 211, a securing mechanism is actuated to draw the noose at least partially into a lumen of the dilator. In some embodiments, at least a portion of the implant within the noose is also drawn into the lumen of the dilator. At 212, the dilator is coupled to a delivery device. At 213, the dilator is delivered to a pelvic region of a patient. At 214, the dilator is passed through a selected tissue portion within the pelvic region. At 215, at least a portion of the implant is deposited within the selected tissue portion. At 216, the dilator is detached from at least a portion of the implant and removed from the patient's body.

Figure 33:
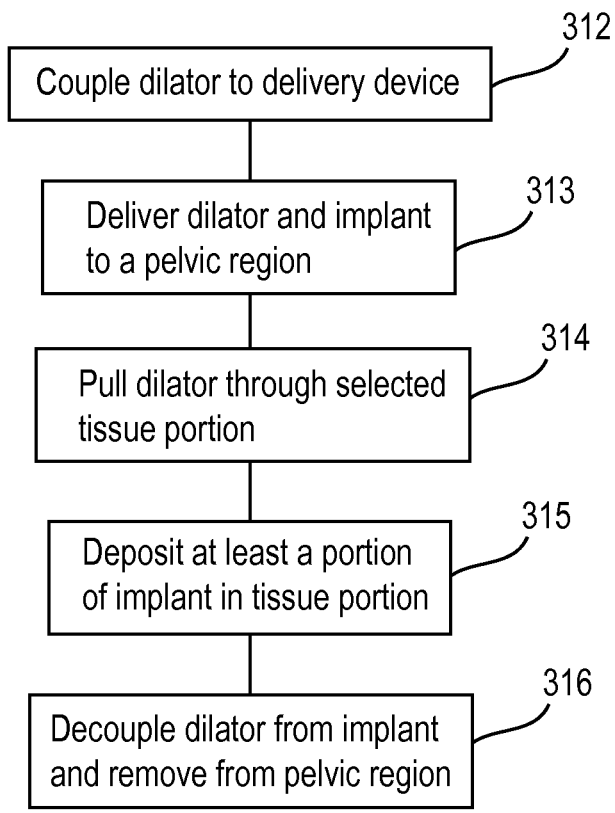

FIG. 33 is a flowchart of another method of delivering an implant to a pelvic region. In this method, an implant can be provided to a physician (or other medical practitioner) pre-assembled to a dilator eliminating the need to secure the implant to one or more dilators prior to implantation. Any of the various embodiments described herein can be provided pre-assembled.

The various components of the dilator devices (e.g., 130, 230, 330, etc.) described herein can be formed with a variety of different biocompatible plastics and/or metals. For example, the elongate body and/or tubular member of the dilator devices can be formed with a polymer. In addition, the elongate body and tubular member of the dilator devices can be formed with a molding or extrusion process. The sutures can be any suitable suture material used for such medical procedures.

The dilator devices described herein can be used to deliver and place a variety of different implants not specifically described. The implants described herein (e.g., implant, 20, 120, 220, etc.) can be formed with a variety of different materials, such as biocompatible plastics and/or metals. In some embodiments, the implant is formed with a mesh material to promote tissue in-growth. For example, Advantage® Mesh manufactured by Boston Scientific Corporation can be used. Alternatively. the implant can be formed with Polyform® mesh material manufactured by Boston Scientific Corporation. The implant can also be formed with materials such that it is disposable. For example, the implant can be formed with materials such that a single use of the device is contemplated.

In one embodiment, an apparatus includes an elongate body that defines a lumen and a suture is coupled to the elongate body and is at least partially disposed within the lumen of the elongate body. The suture extends at least partially from a proximal end of the elongate body and forms a loop configured to couple a portion of a pelvic implant to the elongate body. In some embodiments, the elongate body and the suture collectively form a ratchet mechanism configured to couple the loop to the pelvic implant. In some embodiments, the elongate body defines an opening through a wall and a portion of the suture extends through the opening. In some embodiments, the elongate body defines a first opening and a second opening through a wall of the elongate body. In such an embodiment, a first portion of the suture extends through the first opening, and a second portion of the suture extends through the second opening and is coupled to the first portion of the suture. In some embodiments, the loop forms a portion of a noose around the pelvic implant and the elongate body and the suture are collectively configured to tighten the noose around the pelvic implant. In some embodiments, the loop is configured to receive a portion of a pelvic implant therethrough. In some embodiments, the suture is configured to draw a portion of the pelvic implant into a lumen defined by the elongate body. In some embodiments, the portion of the suture forms a pulley that is configured to draw a portion of the pelvic implant into a lumen defined by the elongate body.

In some embodiments, the apparatus further includes a trocar coupled to a distal end of the suture that is configured to releasably couple the elongate body to a delivery device. In some embodiments, a distal end portion of the suture forms a loop connector configured to releasably couple the elongate body to a delivery device. In some embodiments, the apparatus further includes a connector disposed at a distal end portion of the elongate body that is configured to releasably couple the elongate body to a delivery device.

In another embodiment, a method includes placing a portion of a pelvic implant through a loop of a dilator device. The loop is formed by a suture coupled to an elongate body and a portion of the suture extends at least partially through an opening defined by a wall of the elongate body. The method also includes securing the pelvic implant to the elongate body by moving the portion of the suture relative to the elongate body. In some embodiments, the method includes drawing the portion of the pelvic implant at least partially within a lumen defined by the elongate body. In some embodiments, the method includes drawing the portion of the pelvic implant to a location adjacent a proximal end of the elongate body. In some embodiments, the method includes drawing the portion of the pelvic implant at least partially within a lumen defined by the elongate body while securing the pelvic implant to the elongate body. In some embodiments, the method includes drawing the portion of the pelvic implant to a location adjacent a proximal end of the elongate body while securing the pelvic implant to the elongate body. In some embodiments of the method, securing the pelvic implant to the elongate body includes moving the portion of the suture from a first position substantially parallel to the elongate body to a second position that is transverse to the elongate body. In some embodiments of the method, securing the pelvic implant to the elongate body includes moving the portion of the suture in a direction substantially perpendicular to a longitudinal axis of the elongate body. In some embodiments of the method, securing the pelvic implant to the elongate body includes moving the portion of the suture in a direction substantially parallel to a longitudinal axis of the elongate body.

In another embodiment, a method includes coupling a portion of a pelvic implant to a dilator device. The dilator device includes a ratchet mechanism that is configured to releasably couple the pelvic implant to the dilator device. The dilator device is coupled to a delivery device and the delivery device is inserted through a vaginal incision in a patient. A portion of the pelvic implant is deposited in tissue within the pelvic region of the patient. In some embodiments, the method includes tensioning the implant by pulling the dilator device proximally after depositing a portion of the implant in tissue. In some embodiments, the dilator device is a first dilator device, and the method further includes coupling a second dilator device to the pelvic implant prior to inserting the delivery device through the vaginal incision. In some embodiments, the dilator device is a first dilator device, and the method further includes coupling a second dilator device to the implant. In some embodiments, the method includes passing the dilator device through the pelvic tissue prior to depositing the portion of the pelvic implant in tissue. In some embodiments, the portion of the pelvic implant is coupled to the dilator device after inserting the delivery device into the pelvic region. In some embodiments, the portion of the pelvic implant is coupled to the dilator device prior to inserting the delivery device into the pelvic region.

In another embodiment, a method includes coupling a portion of a pelvic implant to a dilator device. The dilator device includes an elongate body and a tubular member, and at least a portion of the elongate body is slidably disposed within a lumen of the tubular member. The method also includes slidably moving the tubular member relative to the elongate body such that the tubular member at least partially covers a portion of the pelvic implant. In some embodiments, the method includes passing the dilator device through a selected tissue portion such that at least a portion of the pelvic implant is disposed within the tissue. In some embodiments, the method includes coupling a distal end portion of the dilator device to a delivery device. In some embodiments, the method includes coupling a portion of the dilator device to a delivery device and inserting the delivery device through a vaginal incision and to a selected location within a pelvic region.

In another embodiment, an apparatus includes an elongate body having a distal end that is configured to releasably couple the elongate body to a delivery device. The apparatus also includes a tubular member movably disposed over at least a portion of the elongate body and a coupler that is disposed at a proximal end of the elongate body. The coupler is configured to releasably couple a pelvic implant to the elongate body. The tubular member is configured to be slidably disposed over at least a portion of the pelvic implant when the pelvic implant is coupled to the elongate body. In some embodiments, the tubular member has a first configuration in which a proximal end of the tubular member is disposed adjacent to a distal end of the elongate body and a second configuration in which the proximal end of the tubular member is disposed at a spaced distance from the distal end of the elongate body. In some embodiments, the apparatus includes a trocar coupled to the distal end of the elongate body that is configured to releasably couple the elongate body to the delivery device. In some embodiments, the apparatus includes a stop member that is disposed at a distal end of the elongate body and configured to limit the travel of the tubular member relative to the elongate body. In some embodiments, the coupler includes a loop through which the pelvic implant can be disposed. In some embodiments, the elongate body defines a lumen. In some embodiments, the apparatus includes a flange disposed within a lumen defined by the tubular member that is configured to limit the travel of the tubular member relative to the elongate body. In some embodiments, the apparatus includes a connector at a distal end of the elongate body that is configured to releasably couple the elongate body to a delivery device.

In another embodiment, an apparatus includes a first elongate body and a second elongate body. A first sleeve is coupled to the first elongate body and a second sleeve is coupled to the second elongate body. The apparatus also includes an implant member that has a first end portion and a second end portion. The first end portion is coupled to the first sleeve, and the second end portion is coupled to the second sleeve. The first elongate body and the second elongate body are each configured to be associated to a delivery device that is configured to deposit the implant within pelvic tissue. In some embodiments, the first end portion and the second end portion are coupled to the first sleeve and the second sleeve, respectively, with a heat seal. In some embodiments, the first end portion and the second end portion of the implant each have a tanged portion that is configured to engage the pelvic tissue and help secure the implant within the pelvic tissue. In some embodiments, the apparatus includes a connector at a distal end of the first elongate body that is configured to releasably couple the first elongate body to a delivery device.

CONCLUSION

While various embodiments of the invention have been described above, it should be understood that they have been presented by way of example only, and not limitation. Thus, the breadth and scope of the invention should not be limited by any of the above-described embodiments, but should be defined only in accordance with the following claims and their equivalents.

The previous description of the embodiments is provided to enable a person skilled in the art to make and/or use the invention. While the invention has been particularly shown and described with reference to embodiments thereof, it will be understood by those skilled in art that various changes in form and details may be made therein without departing from the spirit and scope of the invention.

For example, the dilator devices described herein (e.g., 130, 230, 330, etc.) can include various combinations and/or sub-combinations of the components and/or features of the different embodiments described. For example, the connection at the distal end of the dilator devices to associate the dilator to a delivery device can be configured for use with either of the delivery devices described herein, or other delivery devices not specifically described. The dilator devices and delivery devices described herein can also be used to deliver and secure pelvic implants not specifically described herein, such as implants having anchors and or sutures.

An implant according to any of the embodiments can be assembled to a dilator device by a user (e.g., physician) or provided preassembled to the user. The implants and dilator devices can also be delivered using other delivery devices not described herein. The implants described herein are merely examples, as other types of pelvic implants can be coupled to a dilator device as described herein for delivery into a pelvic region of a patient. An implant according to the invention can have a variety of different shapes and sizes, such as for example, circular, square, rectangular, elliptical, oval, diamond shaped, triangular, etc., and can include features such as arms and/or straps.

What is claimed is:
1. An apparatus, comprising:
a first elongate body and a second elongate body;
a first sleeve coupled to the first elongate body, the first sleeve having a top wall and a bottom wall opposite to the top wall;
a second sleeve coupled to the second elongate body;
an implant member having a first end portion and a second end portion, the first end portion coupled to the first sleeve, the second end portion coupled to the second sleeve, the first elongate body and the second elongate body each configured to be associated to a delivery device configured to deposit the implant within pelvic tissue;
a suture configured to couple the first end portion of the implant to the first sleeve, the suture forming a loop portion having a first strand portion and a second strand portion in parallel to the first strand portion, the first strand portion and the second strand portion being disposed within the first sleeve and extending from the first end portion of the implant; and
a portion of the top wall of the first sleeve being coupled to a portion of the bottom wall of the first sleeve between the first strand portion and the second strand portion, wherein the coupling of the portion of the top wall of the first sleeve to the portion of the bottom wall of the first sleeve maintains a separation between the first strand portion and the second strand portion within the first sleeve.

2. The apparatus of claim 1, wherein the first end portion and the second end portion of the implant each have a tanged portion configured to engage the pelvic tissue and help secure the implant within the pelvic tissue.

3. The apparatus of claim 1, further comprising:
a connector at a distal end of the first elongate body configured to releasably couple the elongate body to a delivery device.

4. The apparatus of claim 1, the suture being a first suture, further comprising:
a second suture having a first portion and a second portion, the first portion of the second suture being disposed within the second sleeve, the second portion of the suture being woven through a portion of the implant member.

5. The apparatus of claim 1, the suture being a first suture, further comprising:
a second suture having a first portion, a second portion, and a third portion, the first portion of the second suture being disposed within the second elongate body, the second portion being disposed within the second sleeve, and the third portion being coupled to the implant member.

6. The apparatus of claim 1, wherein the first and second strand portions are looped within the first sleeve and weaved through a portion of the implant.

7. The apparatus of claim 1, the suture being a first suture, further comprising:
a second suture extending from the second elongate body and forming a loop, the second suture extending through the second sleeve and being coupled to a portion of the implant member.

8. The apparatus of claim 1, the suture being a first suture and extending from a first end portion of the first elongate body, further comprising:
a second suture extending from a second end portion of the first elongate body and being configured to be associated to the delivery device configured to deposit the implant within pelvic tissue.

9. The apparatus of claim 1, further comprising:
a set of tacks disposed within a distal end portion of the first sleeve, the set of tacks coupling the portion of the top wall of the first sleeve to the portion of the bottom wall of the first sleeve between the first strand portion and the second strand portion; and
a set of secondary tacks disposed at a location proximal to the set of tacks, the set of secondary tacks coupling the first end portion of the implant to the first sleeve between the first strand portion and the second strand portion.

10. The apparatus of claim 1, wherein the first end portion of the implant is also coupled to the first sleeve at a location between the first strand portion and the second strand portion.

11. An apparatus, comprising:
an elongate body;
a sleeve coupled to the elongate body, the sleeve having a top wall and a bottom wall opposite to the top wall;
an implant member;
a suture configured to couple the implant member to the sleeve, the suture being coupled to the elongate body, the suture forming a loop portion having a first strand portion and a second strand portion in parallel to the first strand portion, the first strand portion and the second strand portion extending through a portion of the sleeve, and being coupled to the implant member; and
a portion of the top wall of the sleeve being coupled to a portion of the bottom wall of the sleeve between the first strand portion and the second strand portion, wherein the coupling of the first portion of the top wall of the sleeve to the portion of the bottom wall of the sleeve maintains a separation between the first strand portion and the second strand portion within the sleeve.

12. The apparatus of claim 11, wherein the suture extends from an end portion of the elongate body.

13. The apparatus of claim 11, wherein the loop portion of the suture is woven through a portion of the implant member such that the loop portion of the suture extends from an end of the implant member to a middle portion of the implant member and the suture loops back through the end of the implant.

14. The apparatus of claim 11, the suture being a first suture, the apparatus further comprising:
a second suture coupled to the elongate body.

15. The apparatus of claim 11, the suture being a first suture, the apparatus further comprising:
a second suture coupled to the elongate body, the second suture being configured to be associated to a delivery device configured to deliver the implant member to a location within a body of a patient.

16. The apparatus of claim 11, wherein a portion of the implant member is disposed within the sleeve.

17. An apparatus, comprising:
a first elongate body;
a first sleeve coupled to the first elongate body, the first sleeve having a top wall and a bottom wall opposite to the top wall;
an implant member;
a first suture, the first suture being coupled to a first end portion of the first elongate body, extending through a portion of the first sleeve, and being coupled to a first portion of the implant member, the first suture forming a loop portion having a first strand portion and a second strand portion in parallel to the first strand portion, the first strand portion and the second strand portion extending through the portion of the first sleeve and being coupled to the first portion of the implant member, a portion of the top wall of the first sleeve being coupled to a portion of the bottom wall of the first sleeve between the first strand portion and the second strand portion to maintain a separation between the first strand portion and the second strand portion within the first sleeve;
a second elongate body;
a second sleeve coupled to the second elongate body, the second sleeve having a top wall and a bottom wall opposite to the top wall;
a second suture, the second suture being coupled to the second elongate body, the second suture forming a loop portion extending through a portion of the second sleeve, and being coupled to a second portion of the implant member, the loop portion having a first strand portion and a second strand portion disposed a distance away from the first strand portion, a portion of the top wall of the second sleeve being coupled to a portion of the bottom wall of the second sleeve between the first strand portion and the second strand portion of the loop portion formed by the second suture; and
a third suture extending from a second end portion of the first elongate body, the third suture being disposed apart from the first suture.

18. The apparatus of claim 17, wherein the third suture is configured to be associated to a delivery device configured to deliver the implant member to a location within a body of a patient.

* * * * *